United States Patent
Allen et al.

(10) Patent No.: US 11,131,251 B2
(45) Date of Patent: Sep. 28, 2021

(54) SYSTEM AND METHOD FOR ESTIMATION OF GAS FUEL LOWER HEATING VALUE USING ENERGY BALANCES AND PARAMETRIC ERROR MODELING

(71) Applicant: Solar Turbines Incorporated, San Diego, CA (US)

(72) Inventors: Cody Allen, San Diego, CA (US); Mauricio de Oliveira, San Diego, CA (US)

(73) Assignee: Solar Turbines Incorporated, San Diego, CA (US)

( * ) Notice: Subject to any disclaimer, the term of this patent is extended or adjusted under 35 U.S.C. 154(b) by 326 days.

(21) Appl. No.: 15/852,411

(22) Filed: Dec. 22, 2017

(65) Prior Publication Data

US 2019/0195143 A1 Jun. 27, 2019

(51) Int. Cl.
*F02C 9/28* (2006.01)
*F02C 9/40* (2006.01)
(Continued)

(52) U.S. Cl.
CPC ............. *F02C 9/28* (2013.01); *F02C 9/40* (2013.01); *F23N 1/002* (2013.01); *F23R 3/00* (2013.01); *F05D 2200/11* (2013.01); *F05D 2200/12* (2013.01); *F05D 2200/13* (2013.01); *F05D 2200/14* (2013.01); *F05D 2200/221* (2013.01); *F05D 2220/32* (2013.01); *F05D 2260/81* (2013.01); *F05D 2270/20* (2013.01);
(Continued)

(58) Field of Classification Search
CPC ........ F23N 1/002; F23N 2221/10; F02C 9/28; F05D 2260/81; F23R 13/14; F23R 13/36
See application file for complete search history.

(56) References Cited

U.S. PATENT DOCUMENTS

| 7,058,556 B2 * | 6/2006 | Desai | G05B 17/02 700/31 |
| 7,505,949 B2 * | 3/2009 | Grichnik | G05B 17/02 706/44 |

(Continued)

OTHER PUBLICATIONS

Bryan Li, Mike J. Gross, Thomas P. Schmitt, "Gas Turbine Gas Fuel Composition Performance Correction Using Wobbe Index," POWER2010-27093, Jul. 2009 (Year: 2009).*

(Continued)

*Primary Examiner* — Scott J Walthour
*Assistant Examiner* — David P. Olynick
(74) *Attorney, Agent, or Firm* — Procopio, Cory, Hargreaves & Savitch LLP

(57) ABSTRACT

Systems and methods for improved gas turbine engine performance are disclosed. The method can include receiving an error function for a wide range of fuels. The error function can provide lower heating value (LHV) corrections over the wide range of fuels. The method can include receiving gas turbine engine operation data for a first period of run time on the gas turbine from one or more sensors of the gas turbine engine. The engine operation data can include a performance data points. The method can include determining an optimum LHV based on the engine operation data for the first period of run time and the error function. The method can then include adjusting fuel consumption of the gas turbine engine based on the optimum LHV.

14 Claims, 11 Drawing Sheets

(51) Int. Cl.
  *F23N 1/00* (2006.01)
  *F23R 3/00* (2006.01)
  *G01N 33/22* (2006.01)
  *F23N 5/18* (2006.01)
(52) U.S. Cl.
  CPC .... *F05D 2270/31* (2013.01); *F23N 2005/185* (2013.01); *F23N 2221/10* (2020.01); *F23N 2223/06* (2020.01); *F23N 2223/40* (2020.01); *F23N 2225/04* (2020.01); *F23N 2225/08* (2020.01); *G01N 33/225* (2013.01)

(56) References Cited

U.S. PATENT DOCUMENTS

| | | | | |
|---|---|---|---|---|
| 7,950,216 | B2* | 5/2011 | Dooley | F02C 3/20 60/39.463 |
| 8,478,506 | B2* | 7/2013 | Grichnik | B60W 40/00 701/102 |
| 8,731,797 | B2 | 5/2014 | Demougeot et al. | |
| 2010/0042367 | A1* | 2/2010 | Brown | G05B 17/02 702/182 |
| 2011/0146288 | A1 | 6/2011 | Byrd et al. | |
| 2015/0315978 | A1* | 11/2015 | Davies | F02C 9/40 60/773 |
| 2016/0208749 | A1 | 7/2016 | Sivasubramanian et al. | |

OTHER PUBLICATIONS

Richard T. Meyer, Raymond A. DeCarlo, Steve Pekarek, Chris Doktorcik, Gas Turbine Engine Behavioral Modeling, "Journal of Engineering for Gas Turbines and Power," Dec. 2015, vol. 137. (Year: 2015).*

Chiesa, P., Lozza, G., and Mazzocchi, L., 2005. "Using hydrogen as gas turbine fuel". Transactions of the ASME-A-Engineering for Gas Turbines and Power, 127(1), pp. 73-80.

Rainer X. Kurz, S. M., 2012. "Important properties for industrial gas turbine fuels". Pipeline and Gas Journal, 239(6).

Changdong Sheng, J. A., 2004. "Estimating the higher heating value of biomass fuels from basic analysis data". Biomass and Bioenergy(28).

T. Cordero, F. Marquez, J. R.-M. J. R., 2001. "Predicting heating values of lignocellulosics and carbonaceous materials from proximate analysis". Fuel, 80(11).

Andres Melgar, Juan F. Perez, H. L. A. H., 2007. "Thermochemical equilibrium modelling of a gasifying process". Energy Conversion and Management(48).

S.A. Channiwala, P. P., 2002. "A unified correlation for estimating hhv of solid, liquid and gaseous fuels". Fuel, 81(8).

Demirbas, A., 1997, Estimation of Calorific Values of Fuels from Lignocellulosics, Energy Sources, 19:8, 765-770.

* cited by examiner

SYSTEM AND METHOD FOR ESTIMATION OF GAS FUEL LOWER HEATING VALUE USING ENERGY BALANCES AND PARAMETRIC ERROR MODELING

BACKGROUND

Technical Field

This disclosure relates to improving performance and efficiency of gas turbine engines. More specifically, this disclosure relates to improving fuel management and scheduling with improved estimation of lower heating value (LHV) of the fuels used in gas turbine engines.

Related Art

Gas fuel comes from a myriad of sources, with many molecular composition variations. The energy content, or calorific value of a fuel is expressed in terms of its heating value. Generally, in gas turbine combustion, the gas fuel lower heating value (LHV) is of higher importance. Informally, the LHV of a gas fuel represents a measure of heat that will occur from complete combustion of the given fuel.

In gas turbine fuel control, a common control method is to implement a calculated calorific rate of gas fuel flow into the combustor, which requires pressures, temperatures, effective areas and fuel properties such as LHV and specific gravity (SG). With the calorific flow rate known, the required air mass flow can be calculated to produce the stoichiometric air to fuel ratio in the burner. The engine controller can control guide vanes as well as the fuel control valve(s) to produce this ratio at various loads. A change in gas composition usually leads to a change in gas properties, which produces variation in mass flow rates through the burner, resulting in a change in the calorific flow rate. In particular, variation of the enthalpy drop in expansion occurs as well as variation in the flow rate at the turbine inlet, which propagates through to affect turbine/compressor matching.

LHV and SG may be combined into a single parameter called the Wobbe Index (WI) that provides a measure of interchangeability of fuel gasses.

$$WI = \frac{LHV}{\sqrt{SG} \text{ air}} \quad (1)$$

The higher a gases' WI, the greater the heating value of the quantity of gas that will flow through an orifice of a given diameter in a given interval of time. It is customary to provide WI without units, even though it has the dimensions [Btu/scf] (British thermal units per standard cubic foot). The usefulness of the WI is that if two different gas fuel compositions have the same WI, the pressure drop in a given fuel system will be the same for both gases and in general direct substitution is possible where no change to the fuel system is required. A general design criterion for WI variation is to require changes in the fuel control system; that is changes to set points or updates to fuel properties, when the WI changes from the initial value for which the controller is calibrated, by 10% or more. Therefore, knowledge of both the LHV and SG are necessary for precise operation of gas turbines, especially when gas fuel supply varies in molecular composition.

In combustion theory, the enthalpy of formation can be defined as the energy released or absorbed when the compound is formed from its elements, where the compound and elements occur at the standard reference temperature and pressure. The enthalpy of formation is generally determined by use of statistical thermodynamics combined with observed spectroscopic data. The enthalpy of combustion, $\bar{h}_{RP}$, is defined as the difference between the enthalpy of the products and the enthalpy of the reactants assuming complete combustion is achieved for a given temperature and pressure, that is, $\bar{h}_{RP} = \Sigma_P n_e \bar{h}_e - \Sigma_R n_i \bar{h}_i$ where the n's correspond to the respective coefficients of the reaction equation giving the moles of reactants and products, per mole of fuel. From this, the heating value can be defined as the magnitude of the enthalpy of combustion. The higher heating value (HHV) is obtained when all the $H_2O$ formed as a result of combustion is in liquid form whereas the lower heating value (LHV) is obtained when all the $H_2O$ formed as a result of combustion takes the form of a gas. The higher heating value exceeds the lower heating value by amount commensurate with the magnitude of energy that would be released were all $H_2O$ in the products condensed into liquid, which is sometimes referred to as the latent heat. Note that the energy characterized by the latent heat is not recovered in the combustion process.

Heating values can be determined in a number of ways, with complexity and accuracy depending on the given method. The heating value of a fuel can be determined experimentally by employing an adiabatic bomb calorimeter, which measures the enthalpy change between reactants and products. Prediction of heating values of lignocellulosics and carbonaceous materials from proximate analysis is another standard procedure. Indeed, another popular method in determining the LHV for biomass fuel is ultimate analysis, where the composition of the biomass in weight percent of carbon, hydrogen and oxygen is found, as well as sulfur and nitrogen, if present. In addition to these methods, there exist correlation based methods that use tables and elemental analysis of fuels.

SUMMARY

This disclosure provides systems and methods for improving fuel management and scheduling with improved estimated LHV. The fuel composition is unknown; therefore, the calculation utilizing the moles of reactants is not practical. Instead, the disclosure presents an approach utilizing energy balances through multiple sections of a gas turbine, yielding an equation containing LHV as an explicit variable. Multiple sections are included so the resulting energy balance equation contains only parameters commonly measured on an industrial gas turbine. The disclosure includes a least squares approach to optimization of LHV estimate, and develops a parametric model of the error (error function) of the general energy balance equation across many sets of varied fuel data which produces a global error function. This global error function can then be applied to new sets of data where gas fuel properties are unknown, to estimate LHV to high accuracy.

The systems and methods of the disclosure incorporate a high-fidelity physics-based simulation to build the global error function capable of spanning wide ranges of WI fuels.

An aspect of the disclosure provides a method for operating a gas turbine engine. The method can include receiving a first error function for a plurality of fuels. The method can include receiving, at a fuel controller, first engine operation data for a first period of run time on the gas turbine engine from one or more sensors of the gas turbine engine, the first engine operation data having a plurality of performance data points each referenced to a discrete time. The method can include determining, at the fuel controller, a first lower heating value (LHV) based on the first engine operation data for the first period of run time and the error function. The method can include operating the gas turbine based on the first LHV.

Another aspect of the disclosure provides a device for improved operation of a gas turbine engine. The device can have a memory for storing a first error function for a plurality of fuels. The device can have one or more processors coupled to the memory. The one or more processors can receive first engine operation data for a first period of run time on the gas turbine from one or more sensors of the gas turbine engine, the first engine operation data having a plurality of performance data points each referenced to a discrete time. The one or more processors can determine a first lower heating value (LHV) based on the first engine operation data for the first period of run time and the error function. The one or more processors can adjust a fuel and air mixture supplied to the gas turbine engine based on the first LHV.

Another aspect of the disclosure provides an apparatus for operating a gas turbine engine. The apparatus can have means for receiving a first error function for a plurality of fuels. The apparatus can have means for receiving first engine operation data for a first period of run time on the gas turbine from one or more sensors of the gas turbine engine, the first engine operation data having a plurality of performance data points each referenced to a discrete time. The apparatus can have means for determining a first lower heating value (LHV) based on the first engine operation data for the first period of run time and the error function. The apparatus can have means for operating the gas turbine based on the first LHV.

BRIEF DESCRIPTION OF THE DRAWINGS

The details of embodiments of the present disclosure, both as to their structure and operation, can be gleaned in part by study of the accompanying drawings, in which like reference numerals refer to like parts, and in which.

DETAILED DESCRIPTION

Figure 1:
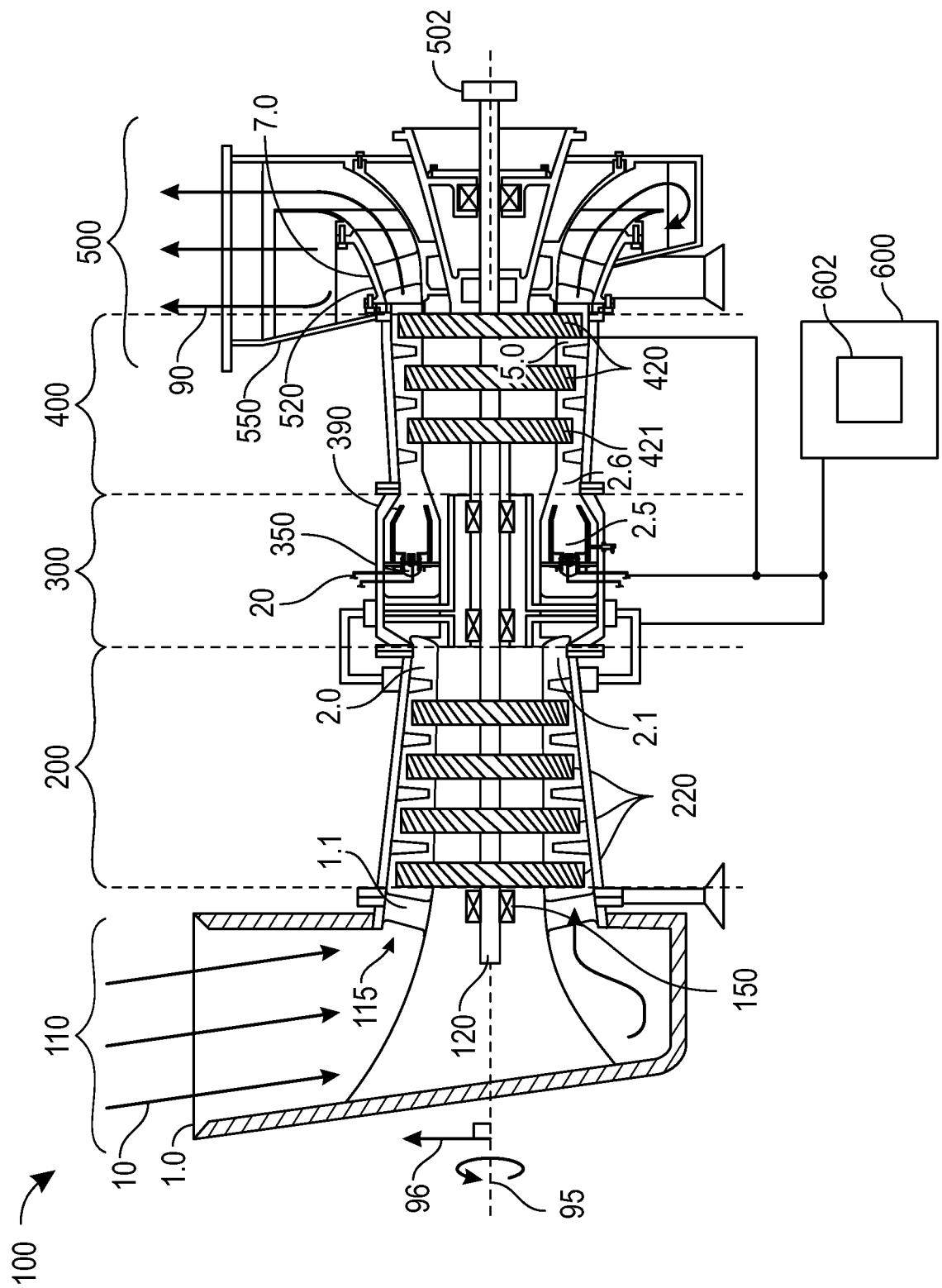
FIG. 1 is a schematic illustration of an exemplary gas turbine engine.

FIG. 1 is a schematic illustration of an exemplary gas turbine engine. Some of the surfaces have been left out or exaggerated (here and in other figures) for clarity and ease of explanation. Also, the disclosure may reference a forward and an aft direction. Generally, all references to "forward" and "aft" are associated with the flow direction of primary air (i.e., air used in the combustion process), unless specified otherwise. For example, forward is "upstream" relative to primary air flow, and aft is "downstream" relative to primary air flow.

In addition, the disclosure may generally reference a center axis 95 of rotation of the gas turbine engine, which may be generally defined by the longitudinal axis of its shaft 120 (supported by a plurality of bearing assemblies 150). The center axis 95 may be common to or shared with various other engine concentric components. All references to radial, axial, and circumferential directions and measures refer to center axis 95, unless specified otherwise, and terms such as "inner" and "outer" generally indicate a lesser or greater radial distance from, wherein a radial 96 may be in any direction perpendicular and radiating outward from center axis 95.

Structurally, a gas turbine engine 100 includes an inlet 110, a gas producer or "compressor" 200, a combustor 300, a turbine 400, an exhaust 500, and a power output coupling 502. The compressor 200 includes one or more compressor rotor assemblies 220. The combustor 300 includes one or more injectors 350 and includes one or more combustion chambers 390. The turbine 400 includes one or more turbine rotor assemblies 420. The exhaust 500 includes an exhaust diffuser 520 and an exhaust collector 550.

As illustrated, both compressor rotor assembly 220 and turbine rotor assembly 420 are axial flow rotor assemblies, where each rotor assembly includes a rotor disk that is circumferentially populated with a plurality of airfoils ("rotor blades"). When installed, the rotor blades associated with one rotor disk are axially separated from the rotor blades associated with an adjacent disk by stationary vanes ("stator vanes" or "stators") 250, 450 circumferentially distributed in an annular casing.

Functionally, a gas (typically air 10) enters the inlet 110 as a "working fluid", and is compressed by the compressor 200. In the compressor 200, the working fluid is compressed in an annular flow path 115 by the series of compressor rotor assemblies 220. In particular, the air 10 is compressed in numbered "stages", the stages being associated with each compressor rotor assembly 220. For example, "4th stage air" may be associated with the 4th compressor rotor assembly 220 in the downstream or "aft" direction (going from the inlet 110 towards the exhaust 500). Likewise, each turbine rotor assembly 420 may be associated with a numbered stage. For example, first stage turbine rotor assembly 421 is the forward most of the turbine rotor assemblies 420. However, other numbering/naming conventions may also be used.

Once compressed air 10 leaves the compressor 200, it enters the combustor 300, where it is diffused and fuel 20 is added. Air 10 and fuel 20 are injected into the combustion chamber 390 via injector 350 and ignited. After the combustion reaction, energy is then extracted from the combusted fuel/air mixture via the turbine 400 by each stage of the series of turbine rotor assemblies 420. Exhaust gas 90 may then be diffused in exhaust diffuser 520 and collected, redirected, and exit the system via an exhaust collector 550. Exhaust gas 90 may also be further processed (e.g., to reduce harmful emissions, and/or to recover heat from the exhaust gas 90).

One or more of the above components (or their subcomponents) may be made from stainless steel and/or durable, high temperature materials known as "superalloys". A superalloy, or high-performance alloy, is an alloy that exhibits excellent mechanical strength and creep resistance at high temperatures, good surface stability, and corrosion and oxidation resistance. Superalloys may include materials such as HASTELLOY, INCONEL, WASPALOY, RENE alloys, HAYNES alloys, INCOLOY, MP98T, TMS alloys, and CMSX single crystal alloys.

The gas turbine engine 100 can have a fuel control system 600. The fuel control system 600 can have a fuel controller 602 having one or more processors operable to control fuel metering or fuel scheduling and overall power output of the gas turbine engine. The fuel control system 600 can receive information from various locations within the gas turbine engine 100. In some embodiments, the fuel control system 600 can receive pressure and temperature information from sensors located in one or more stages within the compressor 200. The fuel controller 602 can also receive information and data from sensors located in one or more stages within the turbine 400 (e.g., turbine gas temperature, turbine inlet temperature, fuel flow, etc.). The fuel control system 600 can also receive information or data from sensors within the combustor 300, such as temperature, fuel flow, fuel pressure, etc. The fuel control system 600 can also receive information related to torque or other measurements of output power at the power turbine, the power output coupling 502, or other power measurement location.

In some embodiments, the fuel control system 600 can use the data collected from various locations within the turbine engine 100 to meter fuel and maximize the output power. The fuel being supplied to the fuel injectors in the combustor 300 may have varying characteristics that may or may not be known. Accordingly, the gas turbine engine 100 may not always be operated at peak or optimal performance. LHV can be a significant factor in peak turbine operation. LHV may also be time-varying, based on the chemical composition of the fuel being supplied. Thus correcting fuel flow or fuel metering, based on LHV over time can provide more efficient and improve gas turbine engine performance. Adjustments to fuel consumption and delivery can be based on the LHV of the fuel in use.

The fuel control system 600 can implement certain machine learning processes to optimize performance and efficiency of the gas turbine engine 100. For example, the fuel control system 600 can implement a hybrid model of the gas turbine engine 100 to maintain peak performance (e.g., optimal efficiency) based on variation of the LHV over time, in combination with an error function. The error function can be generated using machine learning processes applied to a simplified physical model of the gas turbine engine 100 to allow the fuel control system 600 to correct for time-variance of LHV. This can provide an improved operation model for the gas turbine engine 100. The error function can replace a static calibration reference used in fuel control.

Reference is made to FIG. 1 throughout in describing the disclosed system and method for energy balance. Various stations are labeled in FIG. 1 indicating exemplary locations throughout the gas turbine engine 100 where sensor measurements are performed. The sensor measurements can be performed periodically and can be grouped to form a data point, as described below. Each data point can represent a snapshot of engine operating conditions at a specific time. The data points are then used in various calculations in the following described methods.

The following stations listed in Table 1 are referenced in subscripts of the equations in the following description. Some of the station numbers are omitted from the drawing for clarity, however their location within the gas turbine engine 100 should be clear to one of ordinary skill.

TABLE 1

Station Numbers

| Facility | |
|---|---|
| 0.0 | Inlet |
| 9.0 | Exit |
| Compressor/Collector | |
| 1.1 | Inlet flange |
| 2.0 | Outlet Guide Vane (OGV) exit |
| 2.2 | PCD |
| Burner | |
| 2.5 | Inlet |
| 2.6 | Exit |
| Gas Producer (GP) Turbine | |
| 3.0 | First stator inlet |
| 3.1 | First Rotor Inlet |
| 3.2 | Stage 2 stator inlet |
| 3.3 | Stage 2 Rotor inlet |
| Power Turbine | |
| 5.0 | First Stator Inlet |
| 5.1 | First Rotor inlet |
| 5.2 | Stage 2 Stator Inlet |
| 5.3 | Stage 2 Rotor inlet |
| Diffuser/Collector | |
| 7.0 | Diffuser inlet |
| 7.1 | Collector Exit/Flange |
| Recuperator (not shown) | |
| 2.3 | Air inlet |
| 2.4 | Air Exit |
| 7.3 | Gas Inlet |
| 7.5 | Gas Exit |

The following methods for energy balance and fuel control can be performed by one or more processors or microprocessors associated with the fuel controller 602. Such processors or microprocessors can be embodied in a central processing unit (CPU) or, for example, the fuel controller 602. The fuel controller 602 and associated components are described in more detail below in connection with FIG. 14.

The fuel control system 600, or the fuel controller 602 more specifically, can perform various calculations related to energy balance based on fuel characteristics and engine performance data. The fuel control system 600 can further implement certain machine learning techniques in order to execute the following methods. The following is a description of calculations and measurements performed by the fuel control system 600/fuel controller 602 to estimate LHV for improved engine performance.

A simplified energy balance can provide an explicit formulation of LHV. The first law of Thermodynamics, as applied to a 1D control volume with multiple inlets i and outlets e, provides:

$$\frac{dE_{cv}}{dt} = \dot{Q}_{cv} - \dot{W}_{cv} + \sum_i \dot{m}_i \left( h_i + \frac{V_i^2}{2} + gz_i \right) - \sum_e \dot{m}_e \left( h_e + \frac{V_e^2}{2} + gz_e \right)$$

where $\dot{Q}_{cv}$ is the net rate at which energy is being transferred in by heat transfer at time t, and $\dot{W}_{cv}$ is the net rate at which energy is being transferred out by non-flow work at time t. Then at steady state (or quasi-equilibrium):

$$\dot{Q}_{cv} - \dot{W}_{cv} = \sum_e \dot{m}_e \left( h_e + \frac{V_e^2}{2} + gz_e \right) - \sum_i \dot{m}_i \left( h_i + \frac{V_i^2}{2} + gz_i \right) \quad (1)$$

Equation (1) is the basis of the energy balance equation used for engine control (by e.g., the fuel controller 602) in this disclosure. This can be applied to each of the control volumes in the derivation. Note that in the following analyses, the net potential energy, $PE_{net} = \Sigma_e \dot{m}_e z_e - \Sigma_i \dot{m}_i z_i \approx 0$ and is dropped from all calculations. Additionally, the net kinetic energy, $$KE_{net} = \left( \sum_e \dot{m}_e \frac{V_e^2}{2} - \sum_i \dot{m}_i \frac{V_i^2}{2} \right) << \left( \sum_e \dot{m}_e h_e - \sum_i \dot{m}_i h_i \right)$$

and is also dropped from all calculations. Therefore, the approximate energy balance form in the following derivations can be used:

$$\dot{Q}_{cv} - \dot{W}_{cv} = \sum_e \dot{m}_e h_e - \sum_i \dot{m}_i h_i \quad (2)$$

The enthalpy calculation procedures are also applicable. For an ideal gas with constant composition, enthalpy is only a function of temperature, where $$\frac{dh}{dt} = C_p(T) \text{ or } dh = C_p(T)dT.$$

Integration provides, $$h(T_2) = h(T_1) + \int_{T_1}^{T_2} C_p(T) dT$$

In this disclosure, $h(T_1) = h_{ref} = 199.97$ [kJ/kg] and $T_{ref} = 200$ k. Therefore, calculating station enthalpies, results as $$h(T_2) = h_{ref} + \int_{T_{ref}}^{T_2} C_p(T) dT$$

Since integration is a linear operator, superposition provides that this is an equivalent representation of finding the enthalpy change between two arbitrary stations m and n:

$$\int_{T_m}^{T_n} C_p(T) dT = h(T_n) - h(T_m)$$
$$= h(T_n) + (-h_{ref} + h_{ref}) - h(T_m)$$
$$= (h(T_n) - h_{ref}) - (h(T_m) - h_{ref})$$
$$= \int_{T_{ref}}^{T_n} C_p(T) dT - \int_{T_{ref}}^{T_m} C_p(T) dT$$

For each station labeled in FIG. 1 prior to the burner, the only factor is airflow, hence, the specific heat function is that of air alone (e.g., the air 10). The following approximate function for modeling the specific heat of air can be used:

$$C_p(T) = (\beta_0 + \beta_1 T + \beta_2 T^2 + \beta_3 T^3 + \beta_4 T^4) \frac{\bar{R}}{M_{air}}$$

where T is in K and $C_p(T)$ has units [kJ/kg]. The coefficients for specific heat function for air $C_p(T)$ are listed in Table 2.

TABLE 2

List of coefficients for specific heat function $C_p(T)$.

| Coefficient | Value |
|---|---|
| $\beta_0$ | 3.653 |
| $\beta_1$ | $-1.337 \cdot 10^{-3}$ |
| $\beta_2$ | $3.294 \cdot 10^{-6}$ |
| $\beta_3$ | $-1.913 \cdot 10^{-9}$ |
| $\beta_4$ | $0.2763 \cdot 10^{-12}$ |

Energy balance derivations can be initiated by first referencing station numbers from FIG. 1.

Three control volumes (CV) that partition the engine flow paths can then be established. These control volumes can correspond to the compressor 200, the burner or combustor 300, and the turbine 400. These volumes may also be referred to herein as CV compressor, CV burner, and CV turbine, respectively. The subscripts used in the following equations are referenced to FIG. 1 and depict the values or calculations made corresponding to that location in the gas turbine engine 100, as shown in FIG. 1. Based on the control volumes, we have the following relations for mass flows $$\dot{m}_{7.0} = \dot{m}_{3.0} + m_b \quad (3)$$

$$\dot{m}_{3.0} = \dot{m}_{2.0} + m_f \quad (4)$$

$$\dot{m}_{1.0} = \dot{m}_{2.0} + m_b \quad (5)$$

Each subscript indicates a station number for the associated value as noted above in Table 1. For example, $\dot{m}_{3.0}$ is the mass flow at first stator inlet, as shown in FIG. 1.

Regarding the combustor 300, or CV Burner, there is no work other than flow work for this control volume, therefore $\dot{W}_{2,4,3} = 0$.

$$\dot{Q}_{burn} = (\dot{m}_{2.4} + \dot{m}_f) h_{3.0} \dot{m}_{2.4} h_{2.4}$$

The additional heat generated in the burner 300 is a result of the combustion process. The total combustion energy is partially a function of the LHV of the supplied fuel, where the LHV is defined as the amount of heat released by combusting a specified quantity (initially at 25 degrees Celsius) of a fuel and returning the temperature of the combustion products to 150 C, which assumes the latent heat of vaporization of water in the reaction products is not recovered. Therefore, the theoretical heat generated in the burner can be calculated as, $$\dot{Q}_{burn} = \dot{m}_f LHV$$

Using these two quantities, burner efficiency can be determined. For non-recuperated engines, $h_{2.4} = h_{2.0} = h_2$. Burner efficiency is then given by:

$$\eta_b = \frac{\dot{Q}_{actual}}{\dot{Q}_{theoretical}} = \frac{(\dot{m}_{2.4} + \dot{m}_f)h_{3.0} - \dot{m}_{2.4}h_{2.4}}{\dot{m}_f LHV} \quad (6)$$

$$= \frac{\dot{m}_2\left(\left(1 + \frac{\dot{m}_f}{\dot{m}_2}\right)h_3 - h_2\right)}{\dot{m}_f LHV}$$

$$= \frac{\left(1 + \frac{\dot{m}_f}{\dot{m}_2}\right)h_3 - h_2}{\frac{\dot{m}_f}{\dot{m}_2}LHV}$$

$$= \frac{(1+F)h_3 - h_2}{\frac{\dot{m}_f}{\dot{m}_2}LHV} \quad (7)$$

where $$F = \frac{\dot{m}_f}{\dot{m}_2}$$

is the fuel to air ratio in the combustor 300. In the turbine 400, or the CV Turbine, work is produced as a result of the gas flowing through it. Thus, using the energy balance, $$-\dot{W}_{turb} \approx \dot{m}_{7.0}h_{7.0} - (\dot{m}_{3.0}h_{3.0} + \dot{m}_b h_b) \quad (8)$$

$$= \dot{m}_{3.0}\left(\frac{\dot{m}_{7.0}}{\dot{m}_{3.0}}h_{7.0} - h_{3.0} - \frac{\dot{m}_b}{\dot{m}_{3.0}}h_b\right)$$

$$\Leftrightarrow h_3 \approx \frac{\dot{m}_{7.0}}{\dot{m}_{3.0}}h_{7.0} - \frac{\dot{m}_b}{\dot{m}_{3.0}}h_b + \frac{P_{turb}}{\dot{m}_{3.0}}$$

where $\dot{W}_{turb} = P_{turb}$ is total power generated by the turbine 400.

The compressor 200, or CV compressor, consumes work as air 10 is sucked and compressed through it. Using an energy balance, $$\dot{W}_{comp} = \dot{m}_2 h_2 + \dot{m}_b h_b - \dot{m}_1 h_1$$

where $m_b$ is the mass flow that exits the compressor as bleed flow and $h_b$ is the resulting enthalpy of this flow. Then, $$\dot{W}_{comp} \approx \dot{m}_2 h_2 + \dot{m}_b h_b - \dot{m}_1 h_1 \quad (9)$$

$$h_2 \approx \frac{P_{comp}}{\dot{m}_{2.0}} - \frac{\dot{m}_b}{\dot{m}_{2.0}}h_b + \frac{\dot{m}_1}{\dot{m}_{2.0}}h_1$$

Using equations (8) and (9) and the mass flows determined using equations (5), (4), and (3), $$(1+F)h_{3.0} - h_{2.0} \approx (1+F)\left(\frac{\dot{m}_{7.0}}{\dot{m}_{3.0}}h_{7.0} - \frac{\dot{m}_b}{\dot{m}_{3.0}}h_b + \frac{P_{turb}}{\dot{m}_{3.0}}\right) - \quad (10)$$

$$\left(\frac{P_{comp}}{\dot{m}_{2.0}} - \frac{\dot{m}_b}{\dot{m}_{2.0}}h_b + \frac{\dot{m}_1}{\dot{m}_{2.0}}h_1\right) \approx$$

$$(1+F)\left(\frac{\dot{m}_{3.0} + \dot{m}_b}{\dot{m}_{3.0}}h_{7.1} - \frac{\dot{m}_b}{\dot{m}_{3.0}}h_b + \frac{P_{turb}}{\dot{m}_{2.0}+\dot{m}_f}\right) - \frac{P_{comp}}{\dot{m}_{2.0}} +$$

$$\frac{\dot{m}_b}{\dot{m}_{2.0}}h_b - \frac{\dot{m}_{2.0} + \dot{m}_b}{\dot{m}_{2.0}}h_1 = E_P + E_E - E_A + E_b$$

where $$E_P = (1+F)\frac{P_{turb}}{\dot{m}_{3.0}} - \frac{P_{comp}}{\dot{m}_{2.0}} =$$

$$\left(1 + \frac{\dot{m}_f}{\dot{m}_2}\right)\frac{P_{turb}}{\dot{m}_{2.0}+\dot{m}_f} - \frac{P_{comp}}{\dot{m}_{2.0}} = \frac{P_{turb} - P_{comp}}{\dot{m}_{2.0}} = \frac{P_{shaft}}{\dot{m}_{2.0}}$$

$$E_E = (1+F)\frac{\dot{m}_{3.0}+\dot{m}_b}{\dot{m}_{3.0}}h_{7.1} = (1+F)h_{7.1} + (1+F)\frac{\dot{m}_b}{\dot{m}_{3.0}}h_{7.1} =$$

$$(1+F)h_{7.1} + \left(1+\frac{\dot{m}_f}{\dot{m}_2}\right)\frac{\dot{m}_b}{\dot{m}_{2.0}+\dot{m}_f}h_{7.1} = (1+F)h_{7.1} + \frac{\dot{m}_b}{\dot{m}_{2.0}}h_{7.1}$$

$$E_A = \frac{\dot{m}_{2.0}+\dot{m}_b}{\dot{m}_{2.0}}h_1 = h_1 + \frac{\dot{m}_b}{\dot{m}_{2.0}}h_1$$

$$E_b = \frac{\dot{m}_b}{\dot{m}_{2.0}}h_b - (1+F)\frac{\dot{m}_b}{\dot{m}_{3.0}}h_b =$$

$$\frac{\dot{m}_b}{\dot{m}_{2.0}}h_b - \left(1+\frac{\dot{m}_f}{\dot{m}_2}\right)\frac{\dot{m}_b}{\dot{m}_{2.0}+\dot{m}_f}h_b = \frac{\dot{m}_b}{\dot{m}_{2.0}}h_b - \frac{\dot{m}_b}{\dot{m}_{2.0}}h_b = 0$$

It follows that $$(1+F)h_{3.0} - h_{2.0} \approx E_P + E_E - E_A + E_b = \quad (11)$$

$$\frac{P_{shaft}}{\dot{m}_{2.0}} + (1+F)h_{7.1} + \frac{\dot{m}_b}{\dot{m}_{2.0}}h_{7.1} - \left(h_1 + \frac{\dot{m}_b}{\dot{m}_{2.0}}h_1\right) =$$

$$\frac{P_{shaft}}{\dot{m}_{2.0}} + (1+F)h_{7.1} - h_1 + \frac{\dot{m}_b}{\dot{m}_{2.0}}(h_{7.1} - h_1)$$

Accordingly, plugging equation (11) into equation (7) results as:

$$LHV = \quad (12)$$

$$\frac{\left(1+\frac{\dot{m}_f}{\dot{m}_2}\right)h_3 - h_2}{\frac{\dot{m}_f}{\dot{m}_2 \eta_b}} \approx \frac{\frac{P_{shaft}}{\dot{m}_{2.0}} + \left(1+\frac{\dot{m}_f}{\dot{m}_2}\right)h_{7.1} - h_1 + \frac{\dot{m}_b}{\dot{m}_{2.0}}(h_{7.1} - h_1)}{\frac{\dot{m}_f}{\dot{m}_2}\eta_b}$$

A Method for Estimating Lower Heating Value

The balance equation across the burner 300, or CV burner, can be stated as:

$$\eta_b = \frac{\dot{Q}_{actual}}{\dot{Q}_{theoretical}} = \frac{(\dot{m}_{2.4} + \dot{m}_f)h_{3.0} - \dot{m}_{2.4}h_{2.4}}{\dot{m}_f LHV} \quad (13)$$

Using this equation, energy balances for the control volumes through the compressor 200 and the turbine 400 can be approximated:

$$\frac{(\dot{m}_{2.4} + \dot{m}_f)h_{3.0} - \dot{m}_{2.4}h_{2.4}}{\dot{m}_f LHV} \approx \quad (14)$$

$$\frac{\frac{P_{shaft}}{\dot{m}_{2.0}} + \left(1+\frac{\dot{m}_f}{\dot{m}_2}\right)h_{7.1} - h_1 + \frac{\dot{m}_b}{\dot{m}_{2.0}}(h_{7.1} - h_1)}{\frac{\dot{m}_f}{\dot{m}_2}LHV}$$

Equation (14) uses the convention $P_{turbine} = P_{shaft} + P_{compressor} + P_{losses}$, where $P_{losses} \ll P_{shaft} + P_{compressor}$. Written another way, $$LHV = \frac{\frac{P_{shaft}}{\dot{m}_{2.0}} + \left(1 + \frac{\dot{m}_f}{\dot{m}_2}\right)h_{7.1} - h_1 + \frac{\dot{m}_b}{\dot{m}_{2.0}}(h_{7.1} - h_1)}{\frac{\dot{m}_f}{\dot{m}_2}\eta_b} \quad (15)$$

Equation (15) yields a direct solution to solving for the LHV of the fuel. However, there are two unknowns in equation (15), 1) efficiency in the combustor 300, or burner efficiency, $\eta_b$, and 2) LHV. The value of LHV can be determined using a reasonable approximation of $\eta_b$. The reasonable approximation is made to solve for LHV, and further operations are performed in order to correct for any approximation error, as described below. This calculation can be made using a set of N data points. As used herein, the data points refer to a collection (or vector) of sensor measurements made are various stations within the gas turbine engine 100 at a respective time.

Assuming a value for burner efficiency and a set of N data points, results in an over-determined system, where the number of equations exceeds the number of variables. However, a least squares fit to the set of N data points can provide a solution for the value of the optimal LHV. The following quantities can be used:

$$x = LHV$$

$$A = \frac{\dot{m}_f}{\dot{m}_{2.4}}\eta_b$$

$$b = \frac{P_{shaft}}{\dot{m}_{2.4}} + \left(1 + \frac{\dot{m}_f}{\dot{m}_{2.4}}\right)h_{7.1} - h_1 + \frac{\dot{m}_b}{\dot{m}_{2.4}}(h_{7.1} - h_1)$$

Then the problem of solving for LHV takes on the familiar form, $Ax=b$, which has least squares solution. If the columns of A are independent, $A^TA$ is invertible.

$$x = (A^TA)^{-1}A^Tb \quad (16)$$

so that $x = LHV_o$, the optimal LHV, in equation (16). While this yields the optimal LHV in a least squares sense, an error percent ($e_{LS}$) is also present, where:

$$e_{LS} = 100\left(\frac{LHV_o - LHV_{real}}{LHV_{real}}\right) \quad (17)$$

This error percent is due to the approximations made in deriving equation (14).

Error Modeling and More Accurate Estimates of LHV

The previous section describes an energy balance that provided the base calculation for LHV. Then, given N>1 sets of data points, least squares can be used to determine the optimal LHV, or $LHV_o$. However, the percent error, $e_{LS}$, may be larger than acceptable for engineering purposes. Thus, the following provides a method for reducing $e_{LS}$ without altering the approximations needed in equation (14).

In solving $Ax=b$, the optimal x (in the least squares sense), means $\|Ax-b\|_2 = e_{LS}$ is minimized. Therefore, using equation (15), the real LHV value ($LHV_{REAL}$) can be used to minimize errors resulting from approximations (thermodynamic approximations) of various thermodynamic processes of the gas turbine engine 100.

In the scalar case, equation (15), for each set j of data points, let, $$E_j = \left(\frac{P_{shaft}}{\dot{m}_{2.4}} + \left(1 + \frac{\dot{m}_f}{\dot{m}_{2.4}}\right)h_{7.1} - h_1 + \frac{\dot{m}_b}{\dot{m}_{2.4}}(h_{7.1} - h_1)\right)_j \quad (18)$$

$$|e_j| = \left|\left(LHV_{real}\frac{\dot{m}_f}{\dot{m}_{2.4}}\right)_j \eta_b - E_j\right| \geq 0$$

where $e_j$ is the error introduced from thermodynamic approximations used in equation (14) modeling for data set j and not the same as $e_{LS}$. Thus, $|e_j| \geq 0$ for every set of j data.

$$0 = \left(LHV_{real}\frac{\dot{m}_f}{\dot{m}_{2.4}}\eta_b\right)_j - E_j - e_j \quad (19)$$

Returning to matrix form and rearranging equation (18), it can be shown that, $$LHV_{real}\frac{\dot{m}_f}{\dot{m}_{2.4}}\eta_b = \frac{P_{shaft}}{\dot{m}_{2.4}} + \left(1 + \frac{\dot{m}_f}{\dot{m}_{2.4}}\right)h_{7.1} - h_1 + \frac{\dot{m}_b}{\dot{m}_{2.4}}(h_{7.1} - h_1) - e \quad (20)$$

However the goal of this step is to determine an error function, $f(\bullet) = e$. A second order polynomial function can be used, given the shape of modeling errors found in FIG. 3.

$$f(T_1, P_{shaft}) = a_1T_1 + a_2T_1^2 + a_3P_{shaft} + a_4P_{shaft}^2 + a_5T_1P_{shaft} \quad (21)$$

With a definition for $f$, the fuel controller 602 can fit the parameters $a_i$. It is important that the data used to fit the parameters, that is, the "training data", span a plurality (e.g., a wide range) of LHV values and fuel compositions. The "training data" can also span a plurality (e.g., a wide range) of SG values. This can be summed up by spanning a wide range of Wobbe Index values. A wide range of values can be, for example, a range in excess of approximately 200-2300 values. Once this data is collected, estimating each $a_i$ can be accomplished using a least squares estimate. Training data is used in machine learning, when training the system. The coefficients are fit to a given model.

Thus a method for fitting $f$ should proceed as follows. The steps 1-7 outlined below describe the process for creating the error function, $f$.

1. Generate a list of hypothetical fuels, using a predetermined gas-fuel suitability calculation, Certain gas-fuel suitability tools may be particular to a specific turbine engine and may provide information related to suitable fuels for that turbine engine. These fuels are described as "hypothetical" because they correspond to possible fuels selected for use in the gas turbine engine 100. Since fuels may vary widely in chemical composition, gas-fuel suitability tools can provide likely performance characteristics when a given fuel is used. Reference FIG. 9, for example. Each of the hypothetical fuels may correspond with a real world fuel composition. Values for LHV, $LHV_{REAL}$, can be calculated for each hypothetical fuel in the list since the chemical composition is known.
2. Each fuel in the list of hypothetical fuels can be put into a high fidelity model, or simulation, of the gas turbine engine 100, for example. The simulation can provide a full range of theoretical sensor values or sensor measurements (e.g., temperatures, pressure, fuel flow, etc.)

that would be present if the gas turbine engine 100 was burning that fuel. The $LHV_{REAL}$ of each hypothetical fuel can also be an input to the simulation, as LHV is a known value. The full ranges of theoretical sensor values can be exported, for example as a set of data points. Each data point can represent a full set of the theoretical sensor measurements at a given time.

3. Import the set of data points into a scripting language (e.g., Matlab) for modeling.

4. Run the simplified physical model of the gas turbine engine 100 of equation (15) above on the data generated in step (2) using $LHV_{REAL}$ from step (1). This can include determining a point-wise approximation error between $LHV_{REAL}$ and $LHV_{calculated}$ by the simplified physical model. For example, the error ($e_j$) is the difference of the energy balance elements in physics model of equation (18). Using a known fuel composition and the theoretical sensor values, equation 15 provides a solution for LHV at each of t data points (i.e., each data vector corresponds to one "input"). A number t vectors of data provide t values for $LHV_{calculated}$. Therefore, for every t vectors of data, t error values are present: $LHV_{REAL} - LHV_{calculated}(t) = e(t)$.

5. Concatenate all error vectors into a single error vector. This forms an extensive list of $e_j$ for each data point.

6. Put all $T_1$'s and $P'_{shaft}$s into the error function form and concatenate the sets. The result of this step becomes the machine learning training data for the error function, $f$. The wide variation in the fuels used in step (1) can allow the fuel control system 600 (e.g., the fuel controller 602) to learn differences or variations in the fuel and correct the physical model of step (4). The concatenated set of step 6 above refers to the form $A = [T_1\ T_1^2\ P_{shaft}\ P_{shaft}^2\ T_1 P_{shaft}]$ for each set of error vectors.

7. Solve the Ax=b problem for x as above. The variable x is a parameter value for the error function, $f$. The parameter values correspond with the "$a_x$" values in equation (21).

In some embodiments, a single, or global error function, $f$, can be determined to account for the wide range of WI values. However, as described in the following sections, a given error function may not be sufficient to account for all variations in fuel composition. Thus, in some embodiments, more than one error function, $f$, can be used, such as $f_1$ and $f_2$. A global error function is used as a primary example throughout, however two or more error functions can also be used to provide more precise LHV estimates for more efficient engine performance.

Model Corrections

The following is a description of a process for estimating a single LHV. This can allow creation of the error function $f$ proving the accuracy of the LHV calculations. The error function, can then be constructed from a set of varying fuels. LHV can then be calculated using k-fold cross validation.

Estimating LHV from a Single Set of High-Fidelity Data

In a first example, a gas composition may yield $LHV_{real} = 18827$ and SG=0.6748. LHV should be estimated to highest possible degree of accuracy for optimum fuel efficiency and engine performance.

To determine correct values of $W_{2.4}$, bleed flow percentages can be used. As used herein, W is the volumetric air flow entering to combustor 300, after bleed and cooling air have been siphoned off for cooling and bleed. Bleed flow percentages may be derived from the OEM engine documentation, for example. Engine bleed percentages may be fixed or known within a reasonable approximation for a given gas turbine engine 100. Then, $W_{2.4} = WC2 = (1-\text{bleed \%})WC$, where WC is volumetric air flow into the compressor. The fuel controller 602 can then calculate the fuel to air ratio (FAR) based on FAR=WF/WC2 to calculate the true fuel to air ratio in the burner 300.

Figure 2:
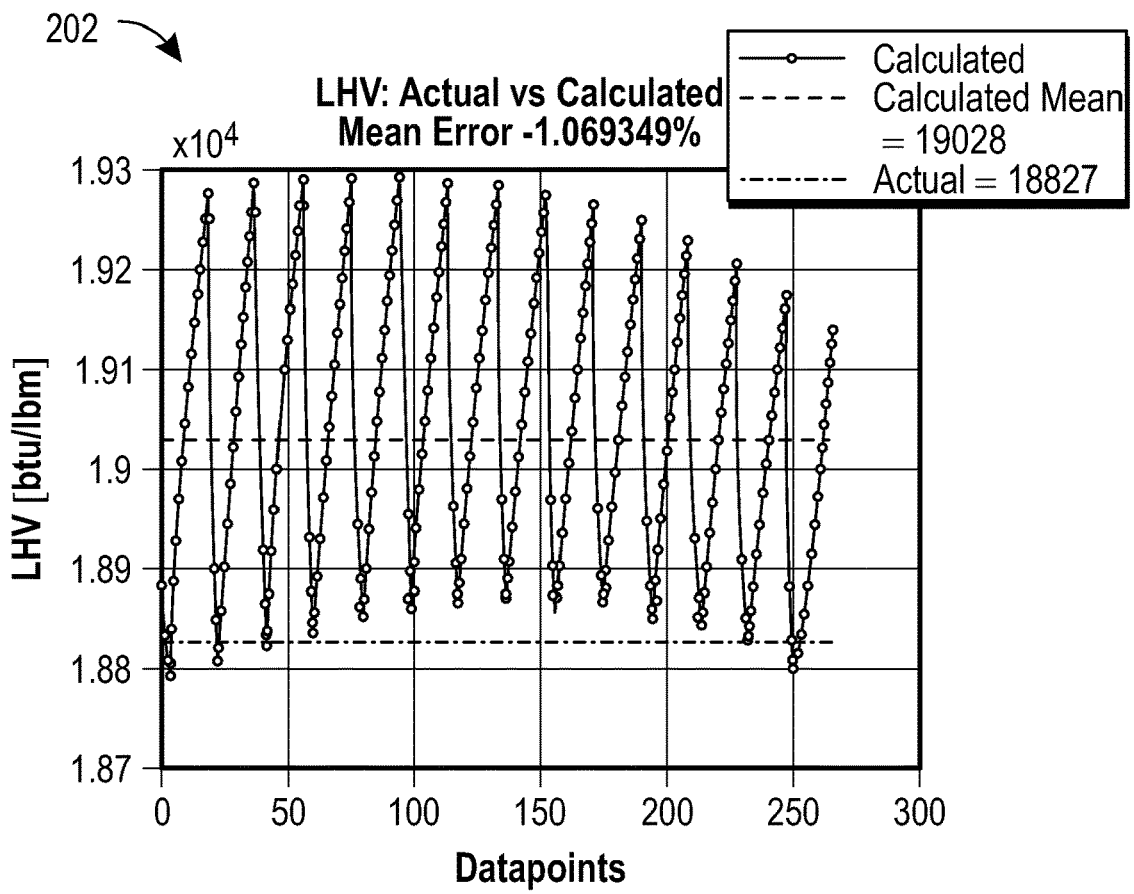
FIG. 2 is a plot diagram of an exemplary LHV calculation performed by the fuel controller 602 of FIG. 1.

FIG. 2 is a plot diagram of an exemplary LHV calculation performed by the fuel controller 602 of FIG. 1. A plot 202 depicts mean error between actual LHV (e.g., $LHV_{REAL}$) and calculated LHV from equation (15). The plot 202 plots LHV in btu/lbm on the vertical axis and a number of data points on the horizontal axis. The plot 202 shows exemplary point wise LHV calculations by the fuel controller 602 from the energy balance equation, equation (15) above. In one example, the actual LHV=18827 [btu/lbm], but the point wise mean value LHV=19028 [btu/lbm]. The fuel controller 602 can calculate the point wise LHV values shown in the plot 202 using the equation (14). Equation (14) can also be used to calculate the point wise error data in the plot 204 (FIG. 4).

This approach may reduce the error somewhat, but the error may still exceed a predetermined threshold. This motivates the least squares calculation described above.

Figure 3:
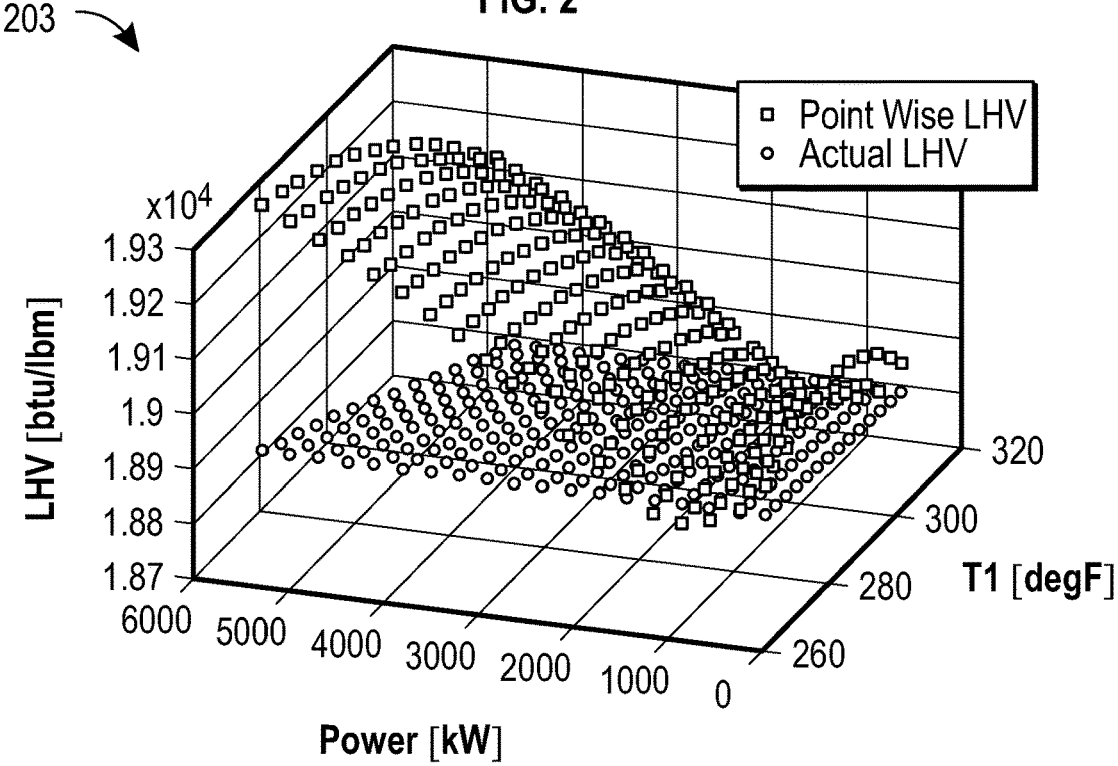
FIG. 3 is a plot diagram of example point wise LHV calculation from energy balance equation.

FIG. 3 is a plot diagram of Example point wise LHV calculation from energy balance equation. Actual LHV=18827 [btu/lbm], and the point wise mean value LHV=19028 [btu/lbm]. A plot diagram 203 shows LHV in btu/bm on the y-axis or ordinate axis, power in kilowatts (kW) on the x or abscissa axis, and temperature (T1) in degrees Fahrenheit on the z-axis or ordinate axis. T1 refers to the temperature at the inlet to the front of the compressor (e.g., station 1.1 of Table 1). As shown, both the T1 and power coordinates have a slight curvature. This feature prompts the use of a quadratic function $f$ in these variables to model the error. This is described in more detail below.

Figure 4:
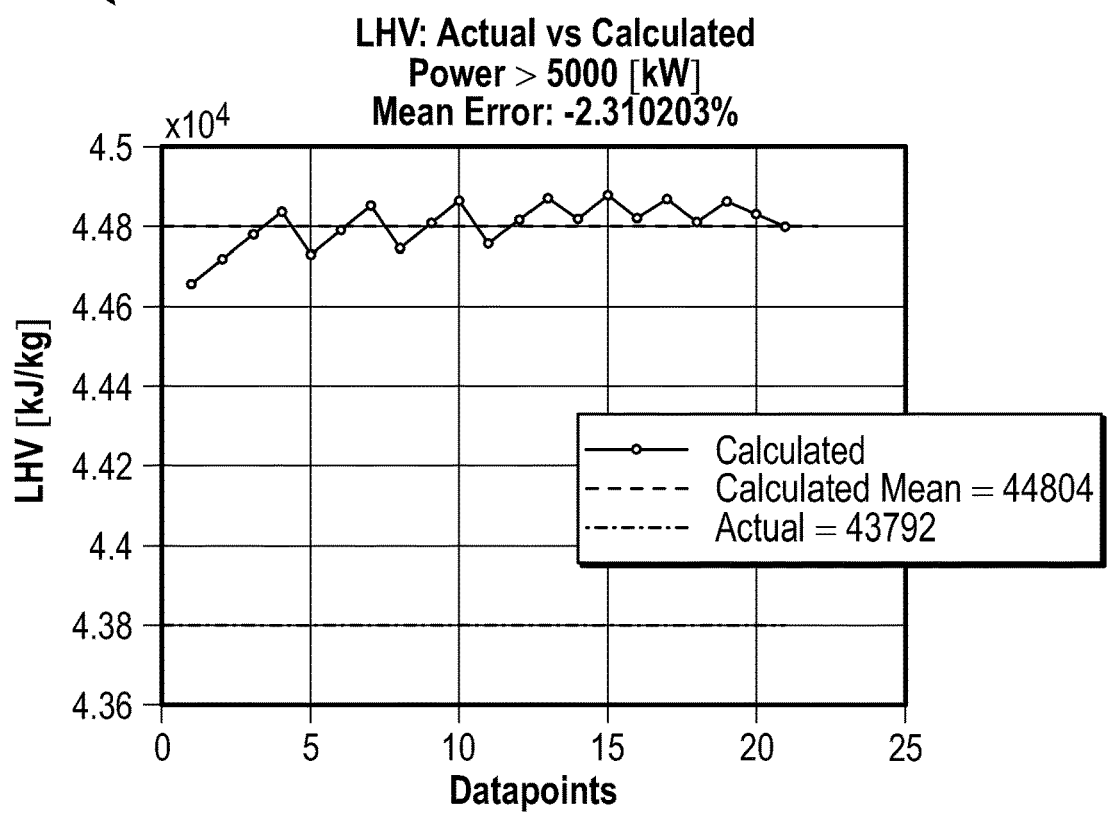
FIG. 4 is a plot diagram of actual versus calculated power in the gas turbine engine of FIG. 1.

FIG. 4 is a plot diagram of actual versus calculated power in the gas turbine engine of FIG. 1. A plot 204 depicts LHV in kJ/kg on the vertical axis and the data points on the horizontal axis. Example point wise LHV calculations can be generated from energy balance equation using only 90%-100% load data points. Actual LHV=43792 [kJ/kg], point wise mean value LHV=44804 [kJ/kg]. The data depicted in FIG. 4 is a representation of the data in the plot 202 filtered for turbine loads above 90% of maximum load.

Figure 5:
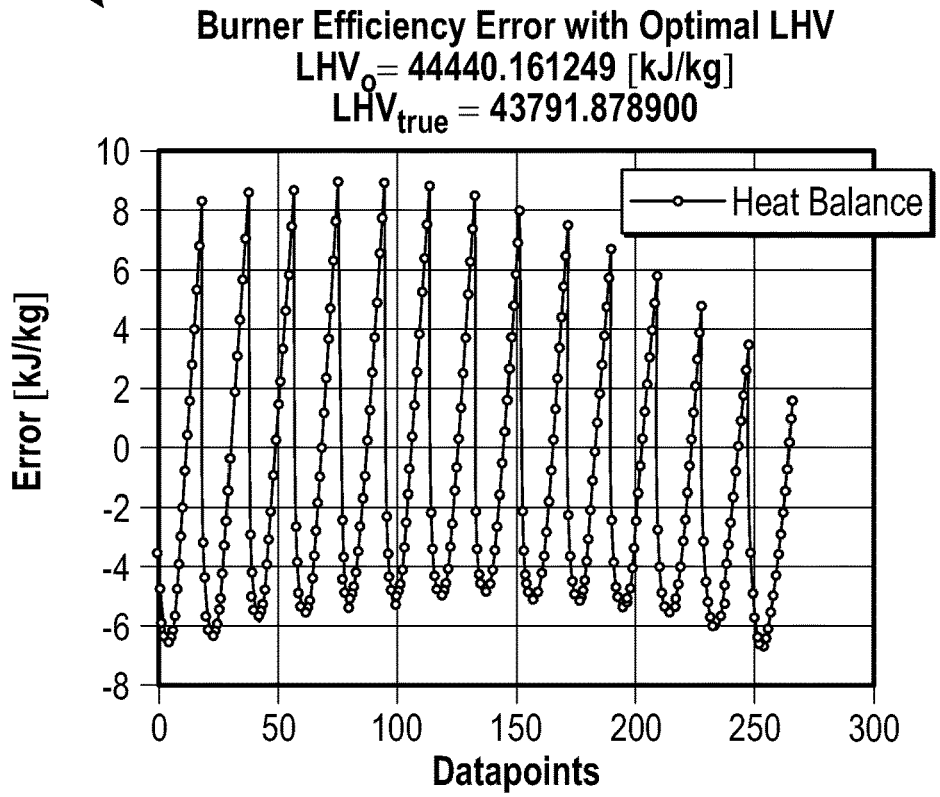
FIG. 5 is a plot diagram of burner efficiency error using optimal LHV in the gas turbine engine of FIG. 1.

FIG. 5 is a plot diagram of burner efficiency error using optimal LHV in the gas turbine engine of FIG. 1. A plot 205 depicts error in kJ/kg (kilojoules per kilogram of fuel) The result of the least squares calculation (described above) is the data shown in the plot 205 of FIG. 5, in which the energy balance error resulting from the least squares fit is shown as a function of sequential data points. The plot 205 of FIG. 5 indicates approximately 1.5% error, for example. However, this may still not provide sufficiently accurate LHV values. The error function can then be used to further reduce the error present in the calculation. This can become particularly valuable when the error function, $f$, is trained across multiple data sets with varying fuel compositions and then applied to a fuel not previously considered.

Figure 6:
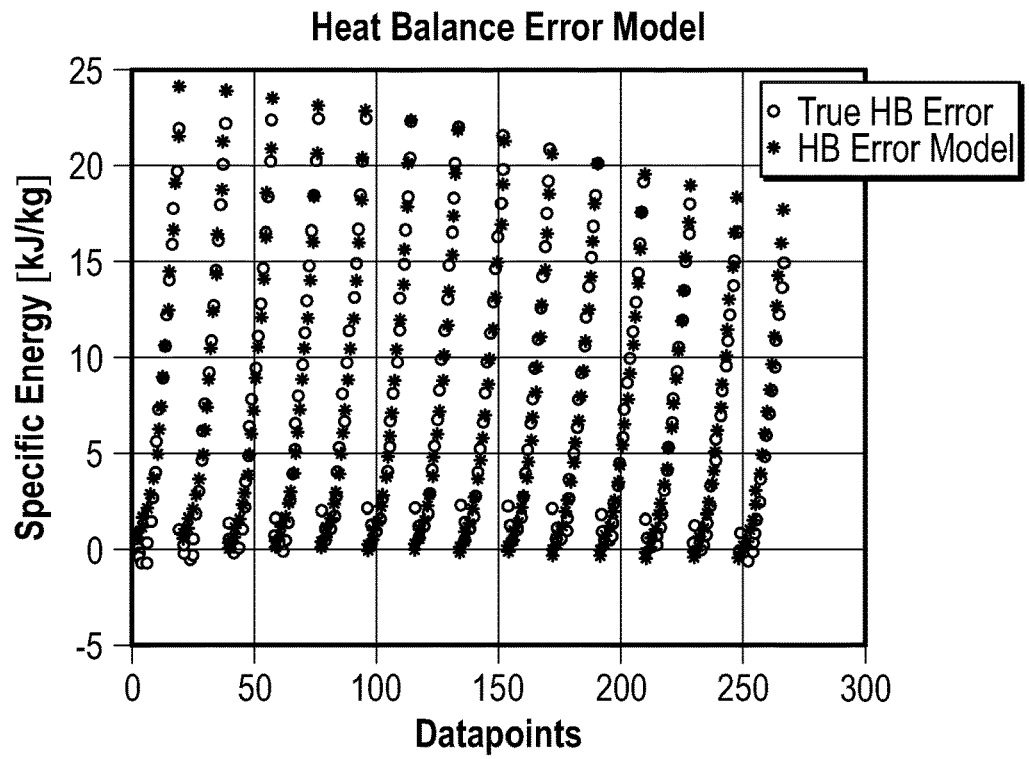
FIG. 6 is a plot diagram of a heat balance error function in the gas turbine engine of FIG. 1.

FIG. 6 is a plot diagram of a heat balance error function in the gas turbine engine of FIG. 1. A plot 206 depicts specific energy in kJ/kg on the vertical axis and the individual data points on the horizontal axis. The plot 206 indicates that the error function can be implemented to accurately approximate heat balance (HB) error resulting from the use of the physics-only model (simplified model). Thus, it can be expected that the error function will further eliminate error in $LHV_{REAL}$ versus s $LHV_O$.

Figure 7:
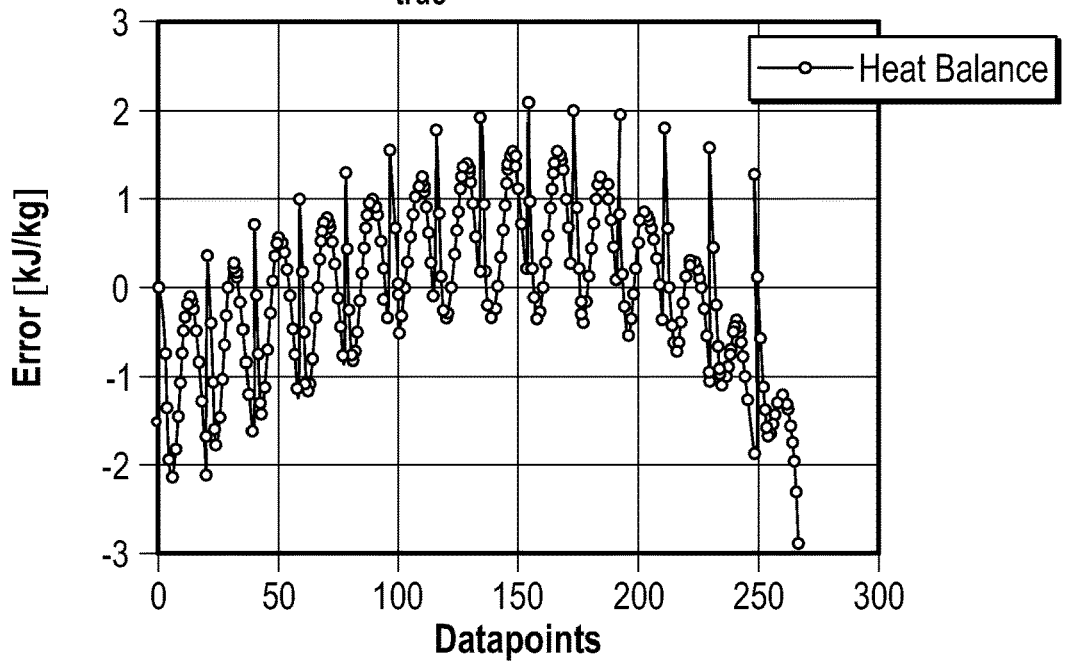
FIG. 7 is a plot diagram of heat balance error using optimal LHV in the gas turbine engine of FIG. 1.

FIG. 7 is a plot diagram of heat balance error using optimal LHV in the gas turbine engine of FIG. 1. A plot diagram 207 depicts error in kJ/kg on the vertical axis versus individual data points on the horizontal axis. The plot 207 is shoes energy balance equation error using $LHV_o$ after $f$ has been applied. In one example, the actual LHV=43791.88 [kJ/kg], while the least squares LHV=43791.54 [kJ/kg], yielding a −0.0013% error. This constitutes a significant error reduction from 1.5% to −0.0767% error.

This approach becomes more valuable when $f$ is applied across multiple data sets with varying fuel compositions. For example, the data sets can include the data from the high fidelity gas turbine engine simulation, where the fuels used in the simulations have varied chemical compositions. Then the fuel controller 602 can apply the same approach to an unknown fuel to optimize power output and efficiency for various unknown fuels.

Applying $f$ Across Varying Fuels

Ideally, a global function $f$ that can account for wide variations in fuel compositions, and specifically, variations in (LHV, SG) pairs is advantageous. As noted above, the function $f$ in equation (21) is, $$f(T_1, P_{shaft}) = a_1 T_1 + a_2 T_1^2 + a_3 P_{shaft} + a_4 P_{shaft}^2 + a_5 T_1 P_{shaft}$$

Figure 8:
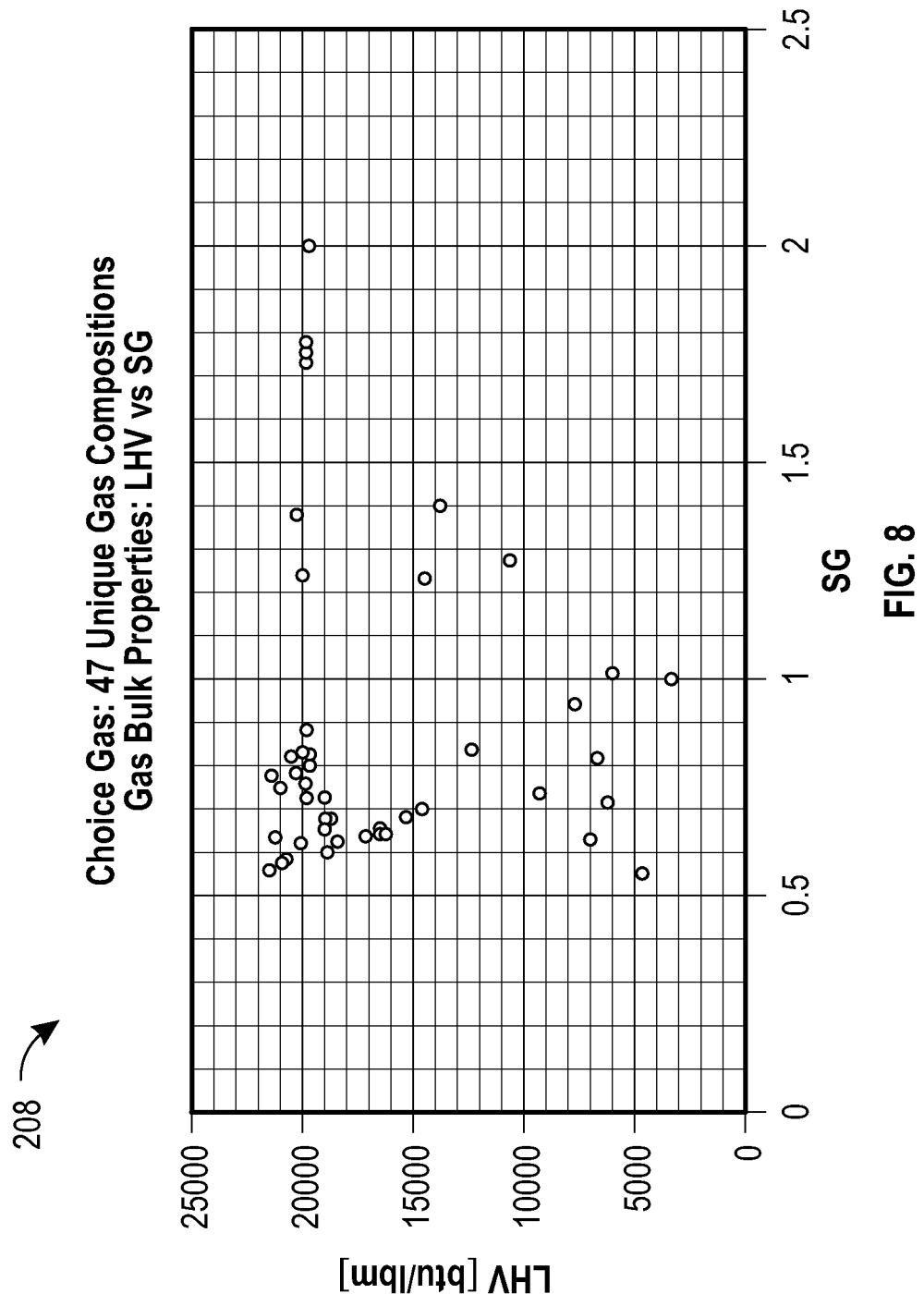
FIG. 8 is a plot diagram of gas bulk properties of 47 exemplary fuel compositions used in the gas turbine engine of FIG. 1.
Figure 9:
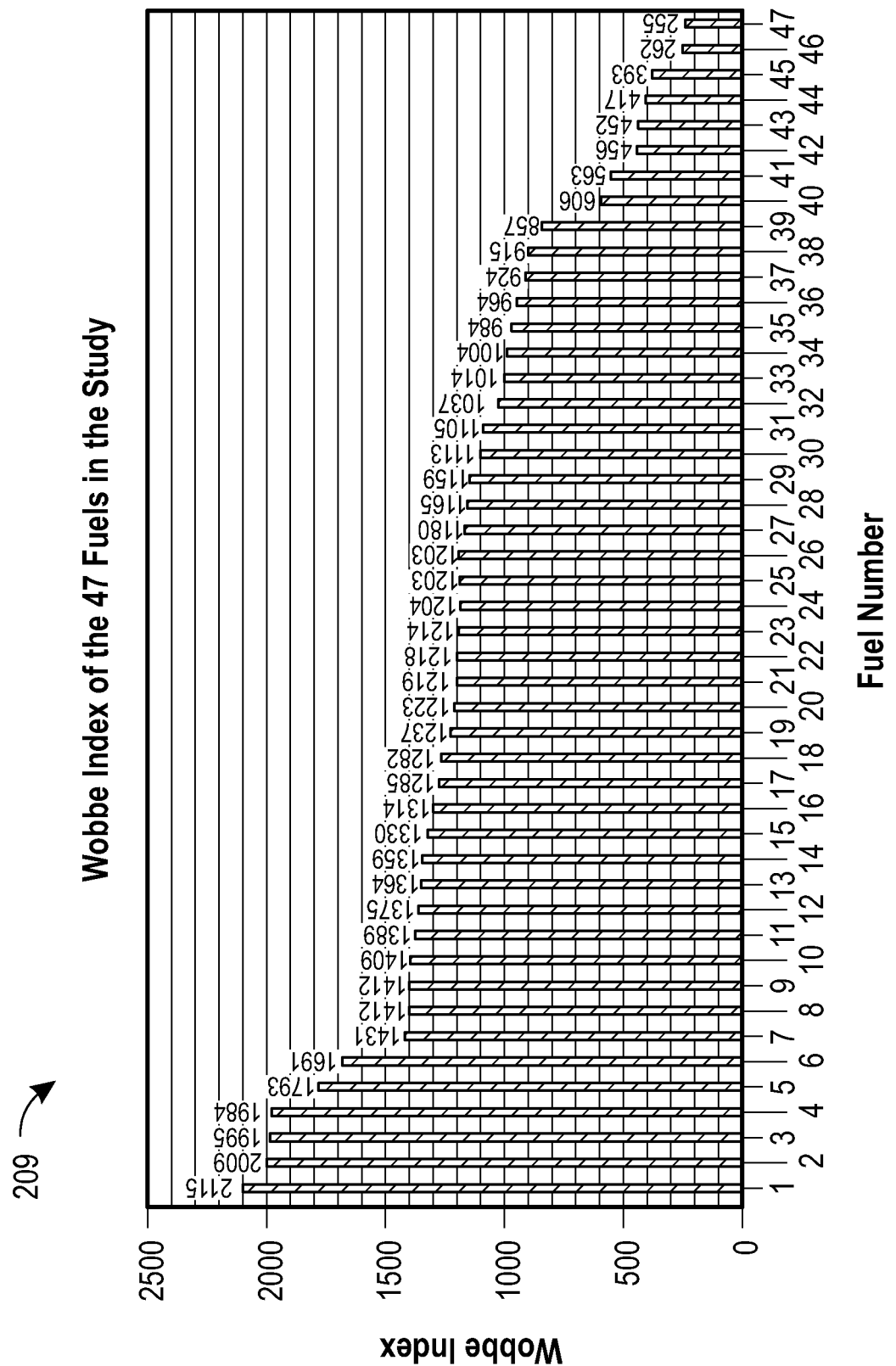
FIG. 9 is a plot diagram of the Wobbe Index of the 47 exemplary fuel compositions of FIG. 8.

Referring briefly to the plot 203 of FIG. 3, it can be seen that the errors have slight quadratic characteristics. This quadratic characteristic is similar across varying fuels. As shown in FIG. 8 and FIG. 9, 47 different exemplary fuel compositions were analyzed using the above described procedures for error reduction.

FIG. 8 is a plot diagram of gas bulk properties of 47 exemplary fuel compositions used in the gas turbine engine of FIG. 1. A plot 208 depicts specific gravity (SG) on the horizontal axis and LHV on the vertical axis for the 47 exemplary fuels used in the "training data" described above. The skilled person will appreciate that the use of these 47 fuels is not limiting on the disclosure. Any number of fuels can be approximated and used for determining the error function as described above. The plot 208 shows the broad cross section of fuels and the wide range of LHV and SG values possible in the fuels provide to and consumed by the gas turbine engine 100, for example. Each of the exemplary fuels may need specific fuel-air mixtures, and therefore specific fuel metering in order to achieve complete combustion in the combustor 300, for example.

FIG. 9 is a plot diagram of the Wobbe Index of the 47 exemplary fuel compositions of FIG. 8. A plot 209 depicts the 47 exemplary fuels along the horizontal axis and the WI (see, equation 1, above) on the vertical axis. As noted above, the 47 fuels are shown by way of example and not limitation. These 47 fuels were used as a basis for a specific study and is not limiting on the disclosure. The plot 209 shows the wide range of WI values, corresponding to the plot 208 and equation (1), above.

In determining the effectiveness of the training data, a global error function $f$ can be used to test against various sets of hold out data. The hold out data is a portion of the random data held away from machine learning training data and used to validate the model (e.g., the error function). For example, four of the fuels are "held out", creating the training data from 43 of the 47 fuels. The remaining four of the fuels can be used to validate the error function. This allows validation of the model based on random data not seen during training.

A k-fold cross validation can be implemented here. For example, 43 of the 47 data sets are used to train $f$, then for the remaining four data sets, calculate $LHV_o$ using $f$ by combining results from equations (16) and (20). For example, a given iteration yields, $$LHV \frac{\dot{m}_f}{\dot{m}_{2.4}} \eta_b = \frac{P_{shaft}}{\dot{m}_{2.4}} + \left(1 + \frac{\dot{m}_f}{\dot{m}_{2.4}}\right) h_{7.1} - h_1 + \frac{\dot{m}_b}{\dot{m}_{2.4}}(h_{7.1} - h_1) - f \quad (22)$$

with the following identifications, $$x = LHV \quad (23)$$

$$A = \frac{\dot{m}_f}{\dot{m}_{2.4}} \eta_b$$

$$\bar{b} = \frac{P_{shaft}}{\dot{m}_{2.4}} + \left(1 + \frac{\dot{m}_f}{\dot{m}_{2.4}}\right) h_{7.1} - ch_1 + \frac{\dot{m}_b}{\dot{m}_{2.4}}(h_{7.1} - h_1) - f$$

and then $$LHV_o = (A^T A)^{-1} A^T \bar{b}$$

The process is completed k−1 more times, each time choosing a new set of four hold out data sets that haven't previously been used. This process can be continued until all engines (e.g., the gas turbine engine 100 from the high fidelity simulations have been used as hold out data. The errors are collected in each of these iterations, for each hold out data set. The results can be collected and graphed, as shown in FIGS. (10) and (11). The median error in performing cross validation is −0.276%.

Figure 10:
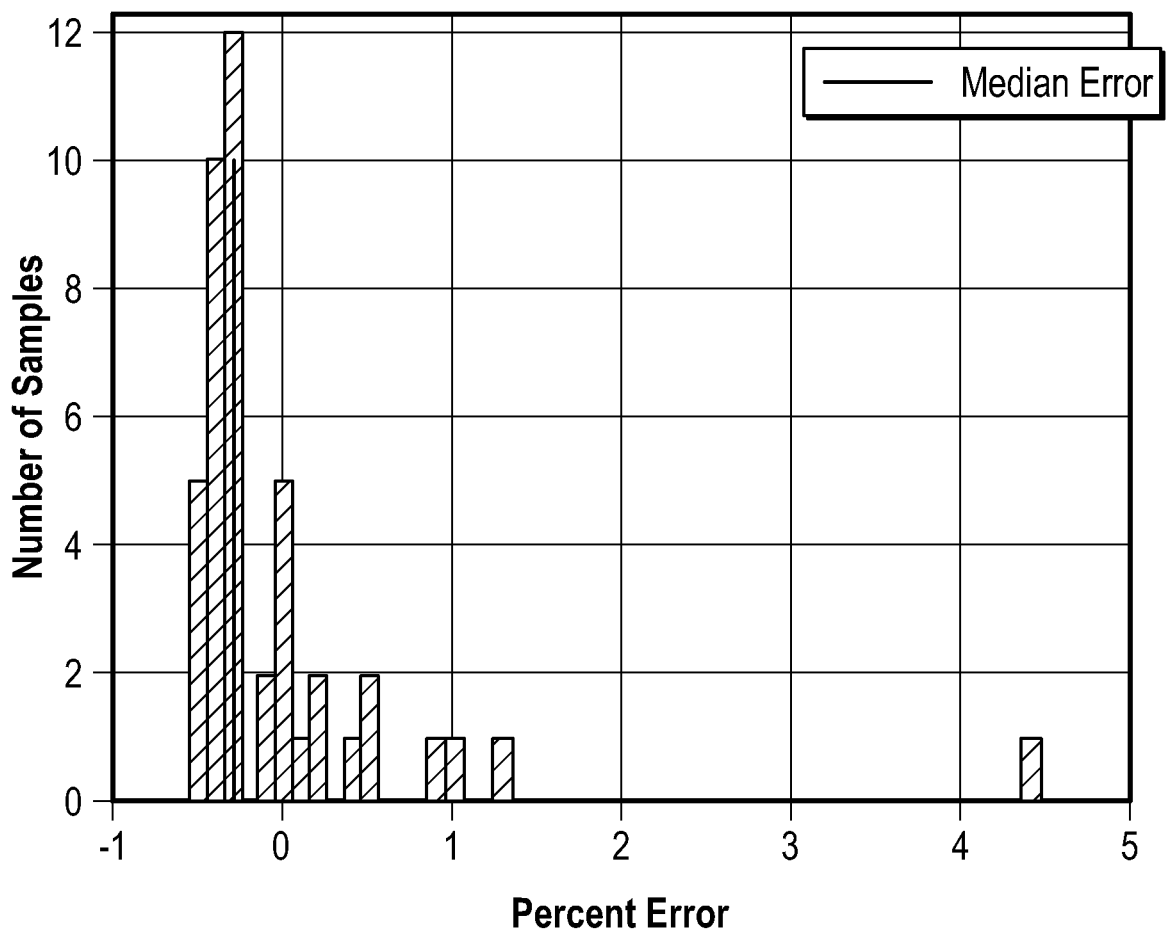
FIG. 10 is a plot diagram of LHV estimates of percent errors versus number of samples of the 47 exemplary fuel compositions of FIG. 8.

FIG. 10 is a plot diagram of LHV estimates of percent errors versus number of samples of the 47 exemplary fuel compositions of FIG. 8. A plot 210 depicts a percent error on the horizontal axis versus a number of samples on the vertical axis. The plot 210 shows validation results of using a global error function, $f$, to calculate optimal LHV. The percent error is calculated as in equation (18) above. K-fold, or 11-fold cross validation is performed to determine testing error (e.g., the error percent). With regard to the one sample with greater than 4% error, the compact distribution about zero (0) provides high confidence in applying $f$, the global error function. In some cases this could be disregarded as a statistical outlier. In some embodiments, this could also be a reason for applying more than one error function to the selected fuels.

Figure 11:
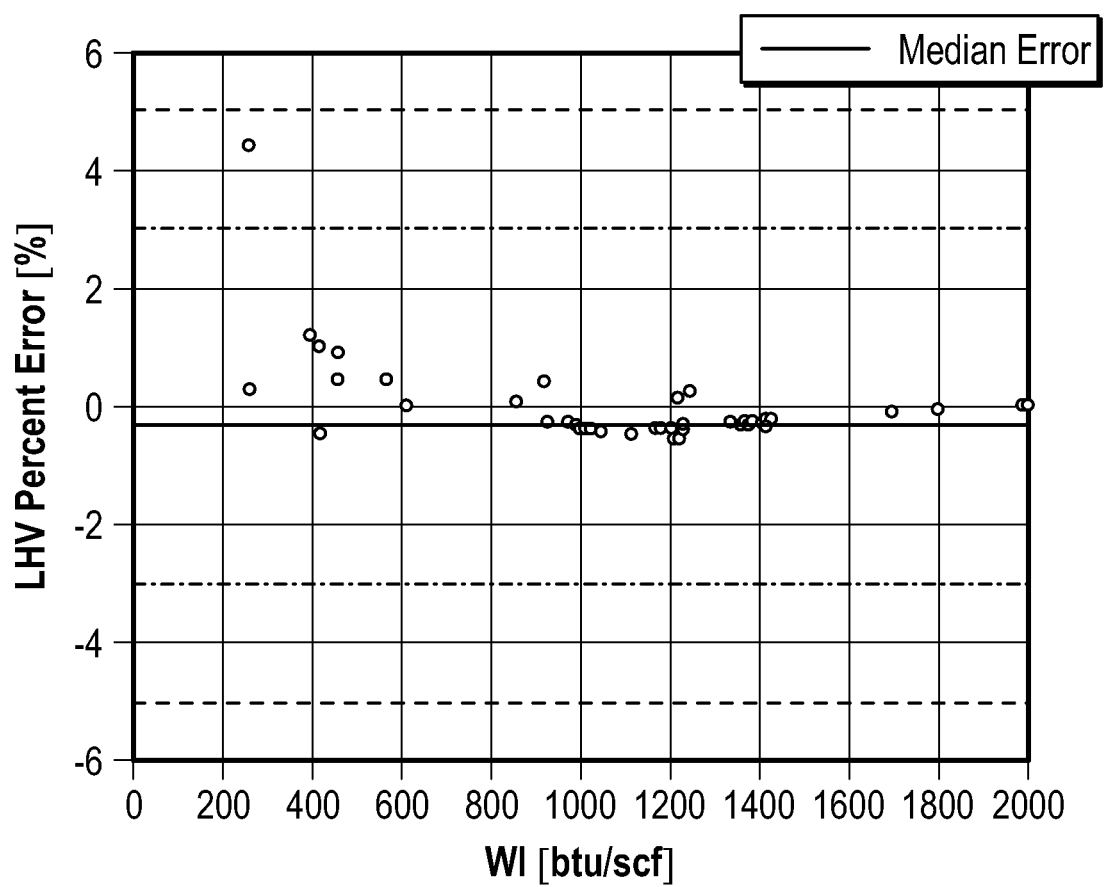
FIG. 11 is a plot diagram of percent error of LHV estimates versus the Wobbe Index of the 47 exemplary fuel compositions of FIG. 8.

FIG. 11 is a plot diagram of percent error of LHV estimates versus the Wobbe Index of the 47 exemplary fuel compositions of FIG. 8. A plot 211 shows WI in btu/scg along the horizontal axis and LHV percent error along the vertical axis. The plot 211 depicts validation results of using the global error function, $f$, to calculate optimal LHVs. Error percent is calculated as in equation (18) and 11-fold cross validation is performed to determine testing error (e.g., the error percent).

Figure 12:
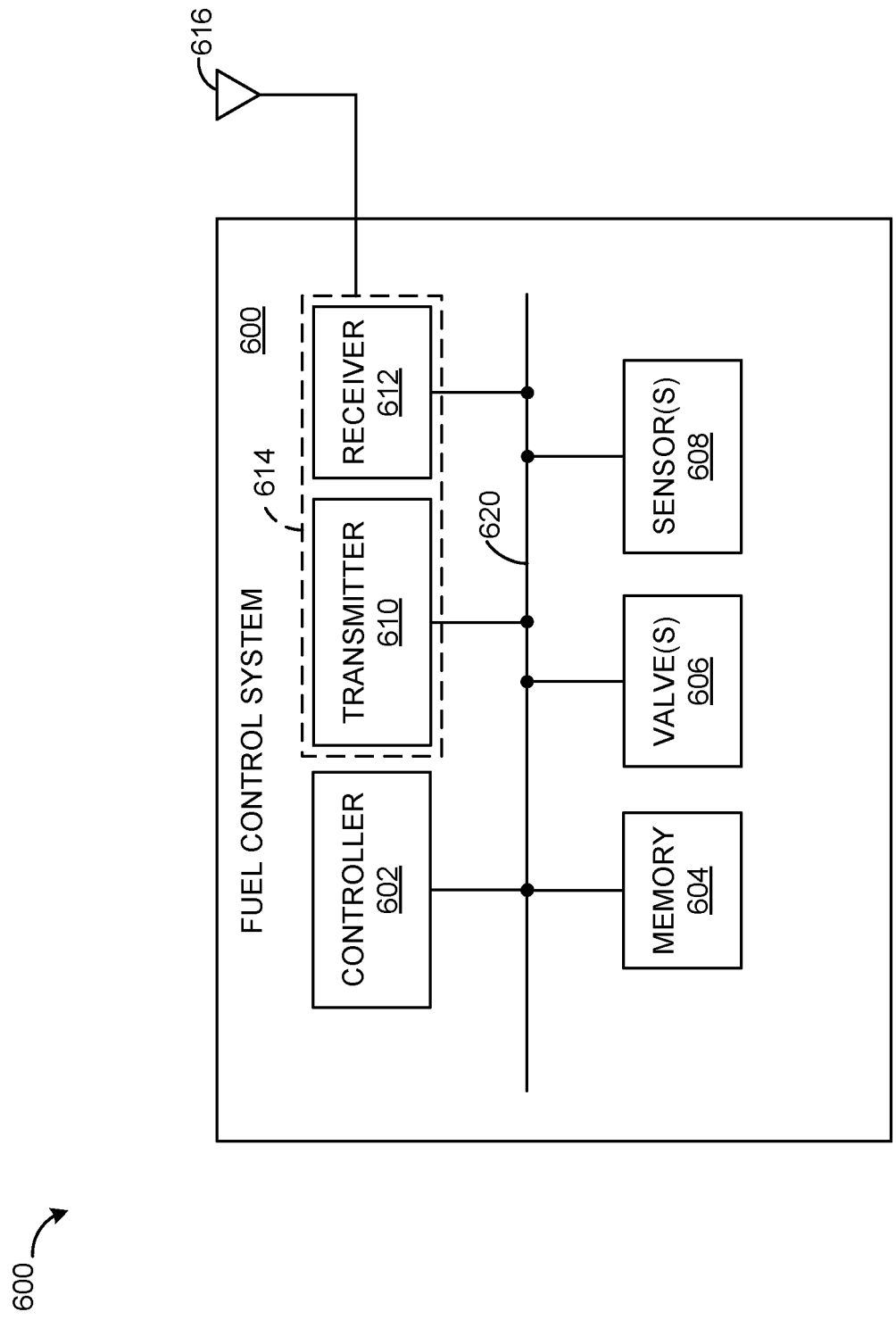
FIG. 12 is a functional block diagram of the fuel control system of FIG. 1.

FIG. 12 is a functional block diagram of the fuel control system of FIG. 1. The fuel control system 600 can be implemented to control fuel metering or fuel delivery and consumption by the gas turbine engine 100. In some embodiments, the fuel control system 600 can also be implemented as an engine control unit (ECU) or form a part of the ECU or other applicable control systems that govern the operation and performance of the gas turbine engine 100. The fuel control system 600 can further be used to perform various functions associated with the gas turbine engine 100 as described in the foregoing description. The fuel control system 600 (or, e.g., the fuel controller 602) can also perform the steps of the methods 800 and 850.

The fuel control system 600 can have the fuel controller (controller) 602. The controller 602 can control operation of the fuel control system 600. The controller 602 can be implemented as one or more processors or microprocessors. The controller 602 may comprise or be a component of a processing system having one or more processors. The one or more processors may be implemented with any combination of general-purpose microprocessors, microcontrollers, digital signal processors (DSPs), field programmable gate array (FPGAs), programmable logic devices (PLDs), controllers, state machines, gated logic, discrete hardware components, dedicated hardware finite state machines, or any other suitable entities that can perform calculations or other manipulations of information.

The fuel control system 600 may further include a memory 604 operably coupled to the controller 602. The memory 604 can include both read-only memory (ROM) and random access memory (RAM), providing instructions and data to the controller 602. The controller 602 can read data from, and write data to the memory 604. A portion of the memory 604 may also include non-volatile random access memory (NVRAM). The controller 602 can perform logical and arithmetic operations based on program instructions stored within the memory 604. The instructions in the memory 604 may be executable to implement the methods described herein (e.g., equations 1-21).

The memory 604 may also include machine-readable media for storing software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the controller 602, cause the fuel control system 600 to perform the various functions described herein.

The controller 602 can be coupled to one or more valves 606. The functional block of the valve 606 represents the fuel delivery/metering function performed by the valves of the gas turbine engine 100. The valves 606 can be configured to control a fuel supply to the combustor 300, for example. The controller 602 can adjust the amount of fuel supplied by opening and closing the valves in order to meter fuel delivered to injectors in the combustor 300, for example. The valves 606 may not be a specific portion of the fuel control system 600, but may be a part of the larger gas turbine engine 100 assembly and communicatively or electrically coupled to the controller 602.

The controller 602 can be coupled to the one or more sensors 608. The sensors 608 can provide various data related to engine performance. For example, the sensors 608 can provide temperature and pressure readings from various locations within the gas turbine engine 100 such as at inlet 110, in the compressor 200, the combustor 300, the turbine 400, or exhaust 500. The sensors 608 can also provide fuel flow information along with other metrics and measurements to the controller 602 for use in the various calculations for determining optimum LHV. The sensors 608 may not be a specific part or component of the fuel control system 600 but are listed as such for ease of description. The sensors 608 may be disposed throughout the gas turbine engine 100.

The fuel control system 600 may also include a transmitter 610 and a receiver 612 to allow transmission and reception of data between the fuel control system 600 and a remote location. For example, such communications may occur between the fuel control system 600 and remote computing systems, for example. The transmitter 610 and receiver 612 may be combined into a transceiver 614. An antenna 616 may be attached to the housing 608 and electrically coupled to the transceiver 614, or to the transmitter 610 and the receiver 612 independently. The fuel control system 600 may also include (not shown) multiple transmitters, multiple receivers, multiple transceivers, and/or multiple antennas.

The various components of the fuel control system 600 described herein may be coupled together by a bus system 620. The bus system 620 may include a data bus, for example, as well as a power bus, a control signal bus, and a status signal bus in addition to the data bus. Those of skill in the art will appreciate the components of the fuel control system 600 may be coupled together or accept or provide inputs to each other using some other mechanism. The fuel control system 600 may provide instructions to the one or more valves 606 and receive information from the sensors 608. The bus system 620 can also transmit and receive or otherwise convey data and information throughout the gas turbine engine 100, and to external systems for data collection or analysis.

Although a number of separate components are illustrated in FIG. 12, one or more of the components may be combined or commonly implemented. For example, the controller 602 may be used to implement not only the functionality described above with respect to the controller 602, but also to implement the functionality described above with respect to the sensors 608, transmitter 610, or the receiver 612, for example. Further, each of the components illustrated in FIG. 12 may be implemented using a plurality of separate elements. Furthermore, the controller 602 may be used to implement any of the components, modules, circuits, or the like described herein, or each may be implemented using a plurality of separate elements.

Figure 13:
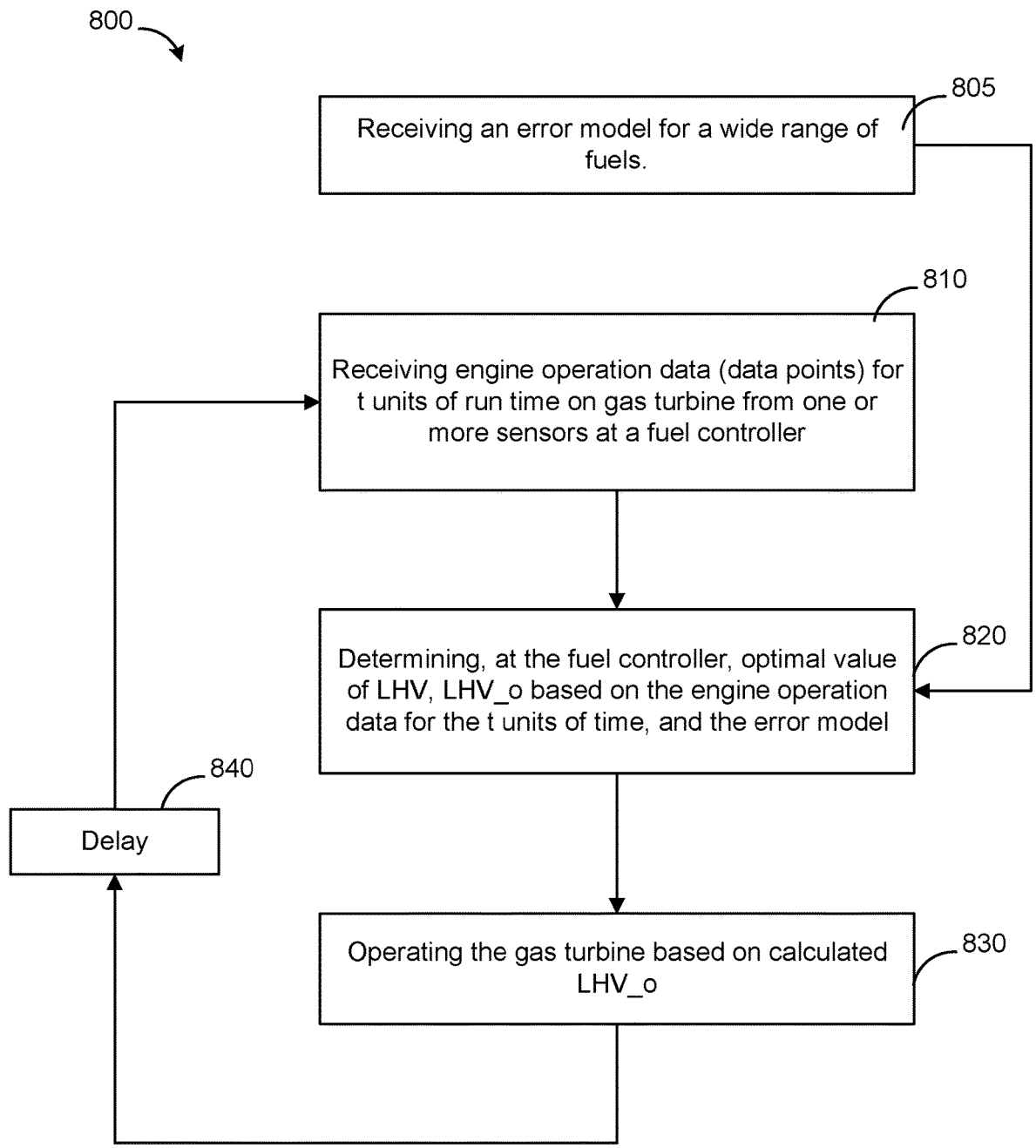
FIG. 13 is a flowchart of a method for improved gas turbine operation.

FIG. 13 is a flowchart of a method for improved gas turbine operation. A method 800 begins at block 805. At block 805, the fuel controller 602 can receive an error function for a wide range of fuels and fuel compositions (reference FIG. 9). The determination of the error function can be similar to the steps 1-7 above, described in connection with FIG. 1. For example, the error function can include a list of hypothetical fuels, describing an anticipated range of chemical composition (step 1). Each of the hypothetical fuels can be input into a high fidelity model of the gas turbine engine 100, for example, to determine theoretical sensor values at a plurality of stations throughout the gas turbine engine 100. The theoretical sensor values can be represented as a set of data points. The actual LHV (e.g., $LHV_{REAL}$) of each of the hypothetical fuels can then be input to a simplified physical model of the gas turbine engine 100 to determine further approximations for engine operating conditions. An approximation error can then be determined between high fidelity model (step 2) and simplified engine model. These errors ($e_j$) can then form the basis for the error function, $f$.

At block 810, fuel controller 602 can receive engine operation data (e.g., fuel consumption data and/or engine performance data) for a period of time. The period of time may be "t-units" of time, where t is a variable or adjustable value. The units can be minutes, hours, or even days. The variation of the t-units of time may be adjusted for more or less frequent changes based on, for example, the type of fuel used in the gas turbine engine 100. The period of time can also be based on the source of the fuel. The quality or components of the fuel used can vary; the t-units can be adjusted to compensate for variation in fuel components to maintain efficient turbine performance. The fuel consumption and engine performance data can be received at the fuel controller 602 from the sensors 608. The engine operation, fuel consumption, and/or engine performance data can be arranged as data points, where each data point has a set of data indicating a collection of engine operating conditions (e.g., sensor data) at a discrete or specific point in time. The gas turbine engine measurements, can include, among other things, shaft power, fuel flow, air flow, inlet temperature, exhaust temperature, bleed/cooling mass flow.

At block 820, the fuel controller 602 can determine an optimal value of LHV for the fuel being consumed based on the fuel consumption and engine performance data during the t-units of time of block 810 and the error function, ƒ. The fuel consumption/engine performance data can be received from the sensors 608 providing real indications of engine operating conditions. The fuel controller 602 can determine the optimum LHV, LHVo, for the t-units of time based on the calculations described above in connection with FIG. 1 through FIG. 11.

At block 830, the fuel controller 602 can overwrite fuel delivery schedules, or adjust the fuel metering or fuel scheduling to the gas turbine engine 100 (e.g., the combustor 300) based on the optimum LHV for the t-units of time. As described above, the LHV of a gas fuel represents a measure of heat that will occur from complete combustion of the given fuel. This can also be considered an amount of energy stored within the fuel. However, the fuel-air mixture within the turbine engine can affect how complete the combustion is within the combustor 300. As fuel composition changes, so does LHV. Therefore the fuel-air mixture may need to be adjusted based on changes to LHV in order to maximize power output or combustion of the fuel. The fuel-air mixture within the gas turbine engine 100 can be modified or adjusted by modifying fuel delivery schedules to maintain complete combustion or near-complete combustion.

At block 840, a delay can be observed before restarting the method 800. The delay can be based on the type of fuel being consumed or supplied to the gas turbine engine 100. The delay can further be based on the t-units of time of block 810. In some embodiments, the method 800 can run continuously. In some embodiments, the step of block 805 can be omitted for iterations of the method 800 following the initial execution. However, if the fuel composition falls outside the expected fuel compositions (e.g., of FIG. 9), new training data may be needed. Accordingly, the method 800 may be restarted at block 805 for a new error function, or error model.

Figure 14:
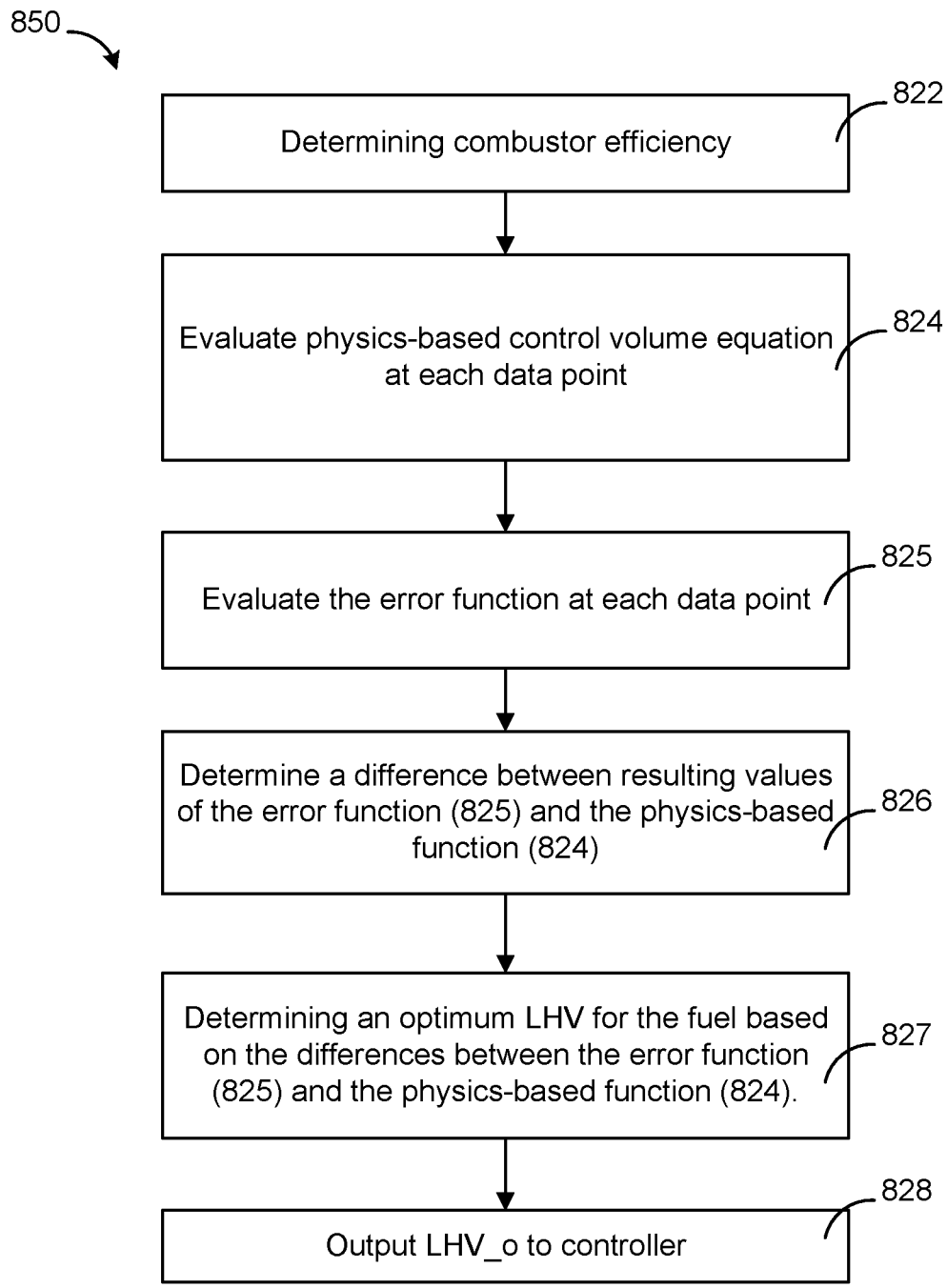
FIG. 14 is a flowchart of a subprocess associated with the method of FIG. 13.

FIG. 14 is a flowchart of a subprocess associated with the method of FIG. 13. In some embodiments, block 820 of the method 800 can be expanded to include multiple sub steps, or sub blocks. A method 850 can be implemented to determine the optimum LHV for use with the gas turbine engine 100.

At block 822, the fuel controller 602 can use the fuel consumption and engine performance data received at block 810 to determine an efficiency of the combustor 300, or a combustor efficiency. The combustor efficiency can be calculated or assumed. Such an assumption can be based on OEM design knowledge and testing. A assumption of efficiency reasonable to the engine can be made.

At block 824, the fuel controller 602 can evaluate the physics-based control volume equation at each data point. This can include determining or solving for variables of the physics-based equation (e.g., equation (23)) based on actual measurements from the sensors 608 (sensor data), for example (e.g., the data points). Specifically, this can include solving for all of the elements of equation (22) except LHV and the error function, ƒ. At block 825, the fuel controller 602 can evaluate the error function at each data point. This can include determining an error value at each data point based on the error function and the sensor data.

At block 826, the fuel controller can determine a difference between the results of the error function (block 825) and the results of the physics-based function (824) using equation (22). The difference can form a matrix of values associated with equation (22) for each data point.

At block 827, the fuel controller 602 can determine an optimum LHV for the fuel in use based on the solution at block 826, for example, by solving the matrix of block 826 for the minimizing LHV value, $LHV_o$. This corresponds to the overdetermined portion of equation (15), above. Thus the fuel controller 602 can determine an optimum LHV during the period of t units of time based on the operating characteristics of the gas turbine engine 100 and the error function.

At block 828, the fuel controller 602 can schedule or meter fuel to the gas turbine engine 100 (e.g., the combustor 300) based on the $LHV_o$. This can also include adjusting fuel metering and air flow for the t units of time.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

[EE Boilerplate] The accompanying claims and their equivalents are intended to cover such forms or modifications as would fall within the scope of the disclosure. For instance, the example apparatuses, methods, and systems disclosed herein may be applied to multi-SIM wireless devices subscribing to multiple communication networks and/or radio access or communication technologies. The various components illustrated in the figures may be implemented as, for example, but not limited to, software and/or firmware on a processor or dedicated hardware. Also, the features and attributes of the specific example embodiments disclosed above may be combined in different ways to form additional embodiments, all of which fall within the scope of the disclosure.

The foregoing method descriptions and the process flow diagrams are provided merely as illustrative examples and are not intended to require or imply that the operations of the various embodiments must be performed in the order presented. As will be appreciated by one of skill in the art the order of operations in the foregoing embodiments may be performed in any order. Words such as "thereafter," "then," "next," etc. are not intended to limit the order of the operations; these words are simply used to guide the reader through the description of the methods. Further, any reference to claim elements in the singular, for example, using the articles "a," "an," or "the" is not to be construed as limiting the element to the singular.

The various illustrative logical blocks, modules, and algorithm operations described in connection with the embodiments disclosed herein may be implemented as electronic hardware, computer software, or combinations of both. To clearly illustrate this interchangeability of hardware and software, various illustrative components, blocks, modules, and operations have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present inventive concept.

The hardware used to implement the various illustrative logics, logical blocks, and modules described in connection with the various embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of receiver devices, e.g., a combination of a DSP and a microprocessor, a plurality of microprocessors, one or more microprocessors in conjunction with a DSP core, or any other such configuration. Alternatively, some operations or methods may be performed by circuitry that is specific to a given function.

In one or more exemplary embodiments, the functions described may be implemented in hardware, software, firmware, or any combination thereof. If implemented in software, the functions may be stored as one or more instructions or code on a non-transitory computer-readable storage medium or non-transitory processor-readable storage medium. The operations of a method or algorithm disclosed herein may be embodied in processor-executable instructions that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include random access memory (RAM), read-only memory (ROM), electrically erasable programmable read-only memory (EEPROM), FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer program product.

Although the present disclosure provides certain example embodiments and applications, other embodiments that are apparent to those of ordinary skill in the art, including embodiments which do not provide all of the features and advantages set forth herein, are also within the scope of this disclosure. Accordingly, the scope of the present disclosure is intended to be defined only by reference to the appended claims.

Those of skill will appreciate that the various illustrative logical blocks (e.g., the various servers described herein), modules, and algorithm steps described in connection with the embodiments disclosed herein can often be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the design constraints imposed on the overall system. Skilled persons can implement the described functionality in varying ways for each particular application, but such implementation decisions should not be interpreted as causing a departure from the scope of the disclosure. In addition, the grouping of functions within a module, block or step is for ease of description. Specific functions or steps can be moved from one module or block without departing from the disclosure.

The various illustrative blocks (e.g., the various functional components herein) described in connection with the embodiments disclosed herein can be implemented or performed with a general purpose processor, a digital signal processor (DSP), application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

The steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium. An exemplary storage medium can be coupled to the processor such that the processor can read information from, and write information to, the storage medium. In the alternative, the storage medium can be integral to the processor. The processor and the storage medium can reside in an ASIC.

It will be understood that the benefits and advantages described above may relate to one embodiment or may relate to several embodiments. The embodiments are not limited to those that solve any or all of the stated problems or those that have any or all of the stated benefits and advantages.

Any reference to 'an' item refers to one or more of those items. The term 'comprising' is used herein to mean including the method blocks or elements identified, but that such blocks or elements do not comprise an exclusive list and a method or apparatus may contain additional blocks or elements.

| Nomenclature | |
|---|---|
| $\dot{Q}_{cv}$ | Net rate of energy transfer by heat across control volume |
| $\dot{W}_{cv}$ | Net rate of energy transfer by work across control volume excluding flow work |
| $KE_{net}$ | Net kinetic energy |
| $PE_{net}$ | Net potential energy |

-continued

| Nomenclature | |
|---|---|
| $\dot{m}_i$ | Total mass flow through inlet i |
| $\dot{m}_e$ | Total mass flow through outlet e |
| $h_i$ | Total specific enthalpy through inlet i |
| $h_e$ | Total specific enthalpy through outlet e |
| $T_n$ | Absolute temperature at station n |
| $c_{p,n}$ | Heat capacity of gas at station n where pressure is constant |
| $P_{section}$ | Power produced or consumed by section |
| $\bar{h}_{RP}$ | Enthalpy of combustion |
| LHV | Lower Heating Value of gas |
| $\eta_b$ | Burner efficiency |
| WI | Wobbe Index |
| F | Fuel to air ratio in burner |
| f | LHV estimation error function |

What is claimed is:

1. A method for operating a gas turbine engine having a shaft, operating in an environment with an ambient temperature and using a fuel with unknown properties, the method comprising:
receiving a global error function $f(T_1, P_{shaft})$, in the form of a polynomial, for a plurality of fuels, wherein $$f(T_1,P_{shaft})=a_1T_1+a_2T_1^2+a_3P_{shaft}+a_4P^2_{shaft}+a_5T_1P_{shaft}$$

and $T_1$ is the ambient temperature, $P_{shaft}$ is power of the shaft $a_1$ and $a_5$ through as are parameters estimated to obtain a best fit on a comparison of lower heating values determined using an energy balance equation versus actual lower heating values across a plurality of sets of historical fuel data for a plurality of fuels, the global error function is used to correct calculated lower heating values;
receiving, at a fuel controller, a first engine operation data for a first period of run time of the gas turbine engine using the fuel with the unknown properties, from one or more sensors of the gas turbine engine, the first engine operation data having a plurality of performance data points each referenced to a discrete time;
calculating, at the fuel controller, a calculated lower heating value (LHV) of the fuel based on a fuel consumption of the gas turbine engine and the first engine operation data for the first period of run time and correcting the calculated LHV with the global error function to generate a first LHV; and
operating the gas turbine engine based on the first LHV.

2. The method of claim 1, wherein the operating the gas turbine engine based on the first LHV further comprises adjusting a fuel and air mixture supplied to the gas turbine engine based on the first LHV.

3. The method of claim 2, wherein the first engine operation data comprises data related to the fuel consumption by the gas turbine engine.

4. The method of claim 2, further comprising,
receiving, after a first delay time, second engine operation data for a second period of run time of the gas turbine engine from the one or more sensors of the gas turbine engine;
calculating, at the fuel controller, a second LHV based on the second engine operation data for the second period of run time and the global error function; and
operating the gas turbine engine based on the second LHV.

5. The method of claim 1, wherein the first engine operation data comprises fuel consumption information.

6. A gas turbine engine which operates in an environment with an ambient temperature and uses a fuel with unknown properties, the gas turbine engine comprising:
a shaft;
a memory for storing a global error function $f(T_1, P_{shaft})$, for a plurality of fuels and one or more processors coupled to the memory and configured to:
receive first engine operation data for a first period of run time of the gas turbine engine using the fuel with the unknown properties, from one or more sensors of the gas turbine engine, the first engine operation data having a plurality of performance data points each referenced to a discrete time;
calculate a calculated lower heating value (LHV) based on the first engine operation data for the first period of run time and correcting the calculated LHV with the global error function $f(T_1, P_{shaft})$ to obtain a first LHV, wherein $$f(T_1,P_{shaft})=a_1T_1+a_2T_1^2+a_3P_{shaft}+a_4P^2_{shaft}+a_5T_1P_{shaft}$$

and $T_1$ is the ambient temperature, $P_{shaft}$ is a power of the shaft, and $a_1$ through $a_5$ are parameters estimated to obtain a best fit on a point-wise error approximation between a real LHV and a calculated LHV for a plurality of possible fuels for use in the gas turbine engine; and
adjust a fuel and air mixture supplied to the gas turbine engine based on the first LHV.

7. The device of claim 6, wherein the first engine operation data comprises data related to fuel consumption by the gas turbine engine.

8. The device of claim 6, wherein the one or more processors is configured to:
receive, after a first delay time, second engine operation data for a second period of run time of the gas turbine engine from the one or more sensors of the gas turbine engine;
calculate, at the fuel controller, a second LHV based on the second engine operation data for the second period of run time and the global error function; and
adjust the fuel and air mixture supplied to the gas turbine engine based on the second LHV.

9. The device of claim 6, wherein the first engine operation data comprises fuel consumption information.

10. An apparatus for operating a gas turbine engine having a shaft, the gas turbine configured to operate in an environment with an ambient temperature and use a fuel with unknown properties, the apparatus comprising:
a memory for storing software instructions; and
a processor coupled to the memory, the processor configured to:
receive first engine operation data for a first period of run time of the gas turbine engine using the fuel with the unknown properties, from one or more sensors of the gas turbine engine, the first engine operation data having a plurality of performance data points each referenced to a discrete time;
calculate a calculated lower heating value (LHV) based on the first engine operation data for the first period of run time and correct the calculated LHV using a global error function $f(T_1, P_{shaft})$ to obtain a first LHV, wherein $$f(T_1,P_{shaft})=a_1T_1+a_2T_1^2+a_3P_{shaft}+a_4P^2_{shaft}+a_5T_1P_{shaft}$$

and T1 is the ambient temperature, $P_{shaft}$ is a power of the shaft, and at through as are parameters estimated to obtain a best fit on a comparison of lower heating values determined using an energy balance equation versus actual lower heating values across a plurality of sets of historical fuel data for a plurality of fuels; and
operate the gas turbine engine based on the first II-V.

11. The apparatus of claim 10, wherein the processor is further configured to adjust a fuel and air mixture supplied to the gas turbine engine based on the first LHV.

12. The apparatus of claim 11, wherein the first engine operation data comprises data related to fuel consumption by the gas turbine engine.

13. The apparatus of claim 11, wherein the processor is further configured to:
- receive, after a first delay time, second engine operation data for a second period of run time of the gas turbine engine from the one or more sensors of the gas turbine engine;
- calculate a second LHV based on the second engine operation data for the second period of run time and the global error function; and
- operate the gas turbine engine based on the second LHV.

14. The apparatus of claim 10, wherein the first engine operation data comprises fuel consumption information.

* * * * *